(12) United States Patent
Hasegawa

(10) Patent No.: US 9,319,129 B2
(45) Date of Patent: Apr. 19, 2016

(54) WIRELESS COMMUNICATION TERMINAL, WIRELESS COMMUNICATION SYSTEM, WIRELESS COMMUNICATION METHOD, AND COMPUTER PROGRAM

(71) Applicant: OLYMPUS CORPORATION, Tokyo (JP)

(72) Inventor: Yasuhiro Hasegawa, Hanno (JP)

(73) Assignee: OLYMPUS CORPORATION, Tokyo (JP)

( * ) Notice: Subject to any disclaimer, the term of this patent is extended or adjusted under 35 U.S.C. 154(b) by 261 days.

(21) Appl. No.: 14/038,183

(22) Filed: Sep. 26, 2013

(65) Prior Publication Data

US 2014/0112227 A1    Apr. 24, 2014

(30) Foreign Application Priority Data

Oct. 18, 2012  (JP) .................. 2012-230949

(51) Int. Cl.
| | |
|---|---|
| *H04B 7/26* | (2006.01) |
| *H04W 12/08* | (2009.01) |
| *H04W 76/02* | (2009.01) |
| *H04W 4/20* | (2009.01) |
| *H04W 88/02* | (2009.01) |
| *H04W 92/18* | (2009.01) |
| *A61B 5/00* | (2006.01) |
| *H04L 29/06* | (2006.01) |

(52) U.S. Cl.
CPC ............. *H04B 7/2612* (2013.01); *H04W 4/206* (2013.01); *H04W 12/08* (2013.01); *H04W 76/023* (2013.01); *A61B 5/002* (2013.01); *H04L 63/108* (2013.01); *H04W 88/02* (2013.01); *H04W 92/18* (2013.01)

(58) Field of Classification Search
CPC .... H04B 7/2612; H04W 4/206; H04W 12/08; H04W 76/023; H04W 88/02; H04W 92/18; A61B 5/002; H04L 63/108
See application file for complete search history.

(56) References Cited

U.S. PATENT DOCUMENTS

| | | | |
|---|---|---|---|
| 8,514,336 B2 * | 8/2013 | Seo ............................... | 348/734 |
| 2009/0045970 A1 * | 2/2009 | Miyabayashi et al. ... | 340/825.22 |

FOREIGN PATENT DOCUMENTS

JP     4618279 B2    1/2011

* cited by examiner

*Primary Examiner* — Melvin Marcelo
(74) *Attorney, Agent, or Firm* — Westerman, Hattori, Daniels & Adrian, LLP

(57) ABSTRACT

A wireless communication terminal, in which a packet for requesting pairing in a data link layer is defined as a pairing request packet, including a wireless communication unit that performs wireless communication with another terminal, a storage device that stores information, a storage control unit that stores first identification data included in a first pairing request packet in the storage device when the wireless communication unit receives the first pairing request packet including the first identification data, a determination section that determines whether the first identification data stored in the storage device and second identification data included in a second pairing request packet satisfy a condition decided in advance when the wireless communication unit receives the second pairing request packet including the second identification data after the first pairing request packet is received.

20 Claims, 13 Drawing Sheets

WIRELESS COMMUNICATION TERMINAL, WIRELESS COMMUNICATION SYSTEM, WIRELESS COMMUNICATION METHOD, AND COMPUTER PROGRAM

BACKGROUND OF THE INVENTION

1. Field of the Invention

The present invention relates to a wireless communication terminal, a wireless communication system, a wireless communication method, and a program.

The present application is based on and claims the benefit of priority from prior Japanese Patent Application No. 2012-230949, filed Oct. 18, 2012, the entire contents of which are incorporated herein.

2. Description of Related Art

In the medical and health care fields, there has been an increased effort to collect biological data from the surface of the human body or the inside of the body using a terminal provided with various sensors, to transmit the biological data collected by the terminal to an accumulation device for accumulation, and use the biological data accumulated in the accumulation device for health management, disease diagnosis, medical treatment, and the like. For this purpose, if the terminal is connected to the accumulation device using a wired cable in order to transmit the biological data, since the freedom of movement is limited, it is preferable to transmit the biological data through wireless communication, and to allow a user to freely carry the terminal. These needs are significantly increased in the medical field, particularly, for an implantable medical device.

In such a wireless communication system, since transmitted/received biological data is individual information, protection of the biological data is necessary. Particularly, demands for the protection are significant in implantable medical devices. Moreover, since the wireless communication system is based on a battery operation, there is a desire to avoid the addition of a hardware configuration which increases battery consumption as much as possible.

As a method in response to such a desire, a pairing method in which a pairing request packet including identification information of its own terminal is transmitted between a remote controller and an electronic device using a predetermined communication channel and wireless communication is started using the communication channel has been disclosed in Japanese Patent Publication No. 4618279.

SUMMARY OF THE INVENTION

According to a first aspect of the present invention, a wireless communication terminal, in which a packet for requesting pairing in a data link layer is defined as a pairing request packet, includes: a wireless communication unit that performs wireless communication with another terminal; a storage device that stores information; a storage control unit that stores first identification data included in a first pairing request packet in the storage device when the wireless communication unit receives the first pairing request packet including the first identification data; a determination section that determines whether the first identification data stored in the storage device and second identification data included in a second pairing request packet satisfy a condition decided in advance when the wireless communication unit receives the second pairing request packet including the second identification data after the first pairing request packet is received; a registration section that registers a terminal, which has wirelessly transmitted the first pairing request packet and the second pairing request packet, as a terminal that wirelessly transmits data of an upper layer above the data link layer when the determination section determines that the first identification data and the second identification data satisfy the condition; and a response section that allows the wireless communication unit to transmit a second pairing response packet to the registered terminal when the determination section determines that the first identification data and the second identification data satisfy the condition, the second pairing response packet indicating a response for the second pairing request packet.

According to a second aspect of the present invention, a wireless communication terminal, in which a packet for requesting pairing in a data link layer is defined as a pairing request packet, includes: a wireless communication unit that performs wireless communication with another terminal; a storage device that stores information; a request section that allows the wireless communication unit to wirelessly transmit a first pairing request packet including predetermined identification data, and then to wirelessly transmit a second pairing request packet including the predetermined identification data; and a registration section that registers a terminal, which has wirelessly transmitted a second pairing response packet, as a terminal that wirelessly transmits data of an upper layer above a data link layer when the wireless communication unit wirelessly transmits the second pairing request packet and then wirelessly receives the second pairing response packet, the second pairing response packet indicating a response corresponding to the second pairing request packet.

According to a third aspect of the present invention, a wireless communication system, in which a packet for requesting pairing in a data link layer is defined as a pairing request packet, includes: a first wireless communication terminal; and a second wireless communication terminal, wherein the first wireless communication terminal includes: a first wireless communication unit that performs wireless communication with another terminal; a first storage device that stores information; a storage control unit that stores first identification data including a first pairing request packet in the first storage device when the first wireless communication unit receives the first pairing request packet including the first identification data; a determination section that determines whether the first identification data stored in the first storage device and second identification data included in a second pairing request packet satisfy a condition decided in advance when the first wireless communication unit receives the second pairing request packet including the second identification data after the first pairing request packet is received; a first registration section that registers a terminal, which has wirelessly transmitted the first pairing request packet and the second pairing request packet, as a terminal that wirelessly transmits data of an upper layer above the data link layer when the determination section determines that the first identification data and the second identification data satisfy the condition; and a response section that allows the wireless communication unit to transmit a second pairing response packet to the registered terminal when the determination section determines that the first identification data and the second identification data satisfy the condition, the second pairing response packet indicating a response for the second pairing request packet, and the second wireless communication terminal includes: a second wireless communication unit that performs wireless communication with another terminal; a second storage device that stores information; a request section that allows the second wireless communication unit to wirelessly transmit a first pairing request packet including predetermined identification data, and then to wirelessly transmit a second pairing request packet including the predetermined identification data; and a second registration section that registers a terminal, which has wirelessly transmitted a second pairing response packet, as a terminal that wirelessly transmits data of an upper layer above a data link layer when the second wireless communication unit wirelessly transmits the second pairing request packet and then wirelessly receives the second pairing response packet, the second pairing response packet indicating a response corresponding to the second pairing request packet.

According to a fourth aspect of the present invention, a wireless communication method, in which a packet for requesting pairing in a data link layer is defined as a pairing request packet, includes: a wireless communication step of performing wireless communication with another terminal; a storage control step of storing first identification data included in a first pairing request packet in a storage device when the first pairing request packet including the first identification data is received in the wireless communication step; a determination step of determining whether the first identification data stored in the storage device and second identification data included in a second pairing request packet satisfy a condition decided in advance when the second pairing request packet including the second identification data is received after the first pairing request packet is received in the wireless communication step; a registration step of registering a terminal, which has wirelessly transmitted the first pairing request packet and the second pairing request packet, as a terminal that wirelessly transmits data of an upper layer above the data link layer when it is determined in the determination step that the first identification data and the second identification data satisfy the condition; and a response step of allowing a wireless communication unit to transmit a second pairing response packet to the registered terminal when it is determined in the determination step that the first identification data and the second identification data satisfy the condition, the second pairing response packet indicating a response for the second pairing request packet.

According to a fifth aspect of the present invention, a wireless communication method, in which a packet for requesting pairing in a data link layer is defined as a pairing request packet, includes: a wireless communication step of performing wireless communication with another terminal; a request step of allowing a first pairing request packet including predetermined identification data to be wirelessly transmitted, and then a second pairing request packet including the predetermined identification data to be wirelessly transmitted in the wireless communication step; and a registration step of registering a terminal, which has wirelessly transmitted a second pairing response packet, as a terminal that wirelessly transmits data of an upper layer above a data link layer when the second pairing request packet is wirelessly transmitted in the wireless communication step, and then the second pairing response packet is wirelessly received in the wireless communication step, the second pairing response packet indicating a response corresponding to the second pairing request packet.

According to a sixth aspect of the present invention, a computer program product embodied on a computer readable device to cause a computer to execute, when a packet for requesting pairing in a data link layer is defined as a pairing request packet: a wireless communication step of performing wireless communication with another terminal; a storage control step of storing first identification data included in a first pairing request packet in a storage device when the first pairing request packet including the first identification data is received in the wireless communication step; a determination step of determining whether the first identification data stored in the storage device and second identification data included in a second pairing request packet satisfy a condition decided in advance when the second pairing request packet including the second identification data is received after the first pairing request packet is received in the wireless communication step; a registration step of registering a terminal, which has wirelessly transmitted the first pairing request packet and the second pairing request packet, as a terminal that wirelessly transmits data of an upper layer above the data link layer when it is determined in the determination step that the first identification data and the second identification data satisfy the condition; and a response step of allowing a wireless communication unit to transmit a second pairing response packet to the registered terminal when it is determined in the determination step that the first identification data and the second identification data satisfy the condition, the second pairing response packet indicating a response for the second pairing request packet.

According to a seventh aspect of the present invention, a computer program product embodied on a computer readable device, the computer program product to cause a computer to execute, when a packet for requesting pairing in a data link layer is defined as a pairing request packet: a wireless communication step of performing wireless communication with another terminal; a request step of allowing a first pairing request packet including predetermined identification data to be wirelessly transmitted, and then a second pairing request packet including the predetermined identification data to be wirelessly transmitted in the wireless communication step; and a registration step of registering a terminal, which has wirelessly transmitted a second pairing response packet, as a terminal that wirelessly transmits data of an upper layer above a data link layer when the second pairing request packet is wirelessly transmitted in the wireless communication step, and then the second pairing response packet is wirelessly received in the wireless communication step, the second pairing response packet indicating a response corresponding to the second pairing request packet.

DETAILED DESCRIPTION OF THE INVENTION

Hereinafter, embodiments of the present invention will be described with reference to the accompanying drawings. It will be apparent to those skilled in the art from this disclosure that the following description of the embodiments of the present invention is provided for illustration only, and not for the purpose of limiting the invention as defined by the appended claims and their equivalents.

(First Embodiment)

Figure 1:
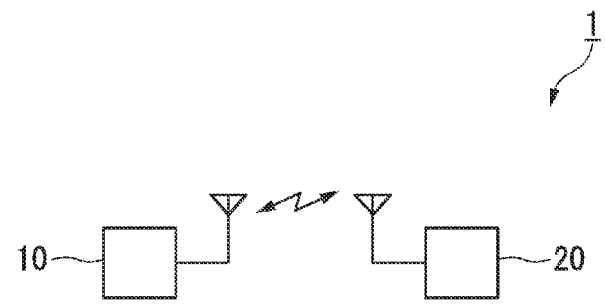
FIG. 1 is a schematic diagram illustrating the configuration of a biological data-monitoring system in a first embodiment of the present invention.

Hereinafter, a first embodiment of the present invention will be described with reference to the accompanying drawings. FIG. 1 is a schematic diagram illustrating the configuration of a biological data-monitoring system in the present embodiment. In the illustrated example, a biological data-monitoring system 1 includes a wireless sensing terminal 10 and a data collection terminal 20.

The wireless sensing terminal 10 acquires biological data such as blood pressure, a pulse, an electrocardiograph, a heartbeat, a blood oxygen level, a body temperature, glycosuria, or blood sugar, from the surface of the human body or the inside of the body using various sensors. The wireless sensing terminal 10 acquires device status data, which indicates the status of each element provided in the wireless sensing terminal 10, using various sensors. The wireless sensing terminal 10 wirelessly transmits the acquired biological data and device status data to the data collection terminal 20. The data collection terminal 20 collects and stores the biological data and the device status data wirelessly transmitted from the wireless sensing terminal 10. The wireless sensing terminal 10 is installed on the surface of the human body or inside the body. The data collection terminal 20 is installed outside of the body.

In the present embodiment, a description will be given on the assumption that the wireless sensing terminal 10 and the data collection terminal 20 wirelessly communicate with each other in a one-to-one manner. However, the present invention is applicable to relations of 1 to N, M to 1, and M to N (N and M are a natural number).

Figure 2:
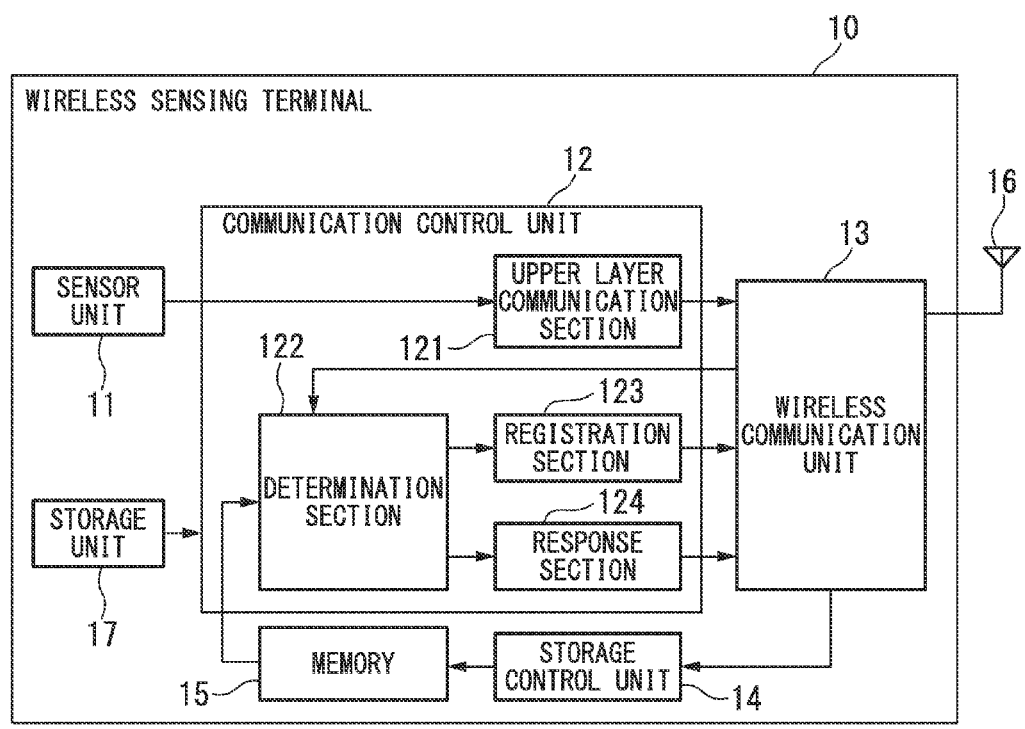
FIG. 2 is a block diagram illustrating the configuration of a wireless sensing terminal in a first embodiment of the present invention.

Next, the configuration of the wireless sensing terminal 10 (a wireless communication terminal or a first wireless communication terminal) will be described. FIG. 2 is a block diagram illustrating the configuration of the wireless sensing terminal 10 in the present embodiment. In the illustrated example, the wireless sensing terminal 10 includes a sensor unit 11, a communication control unit 12, a wireless communication unit 13 (a first wireless communication unit), a storage control unit 14, a memory 15 (a storage device or a first storage device), an antenna 16, and a storage unit 17 (a storage device or a first storage device). The wireless sensing terminal 10 includes a battery (not illustrated). The battery supplies power to each element provided in the wireless sensing terminal 10.

The sensor unit 11 is installed on the surface of the human body or inside the body to acquire the biological data by sensing blood pressure, a pulse, an electrocardiograph, a heartbeat, a blood oxygen level, a body temperature, glycosuria, or blood sugar. The sensor unit 11 acquires the device status data by sensing the status of each element provided in the wireless sensing terminal 10. Hereinafter, the biological data, the device status data and the like acquired by the sensor unit 11 will be referred to as collection data. The sensor unit 11 outputs the collection data to the communication control unit 12.

The storage control unit 14 acquires first pairing information from a first pairing request packet input from the wireless communication unit 13. The storage control unit 14 stores the acquired first pairing information in the memory 15. The memory 15 stores the first pairing information under the control of the storage control unit 14. The memory 15 outputs the stored first pairing information to the communication control unit 12.

The communication control unit 12 includes an upper layer communication section 121, a determination section 122, a registration section 123 (a first registration section), and a response section 124, and controls the wireless communication unit 13. The determination section 122 outputs a first response instruction to the response section 124 when the first pairing information input from the memory 15 has been updated. When the first pairing information input from the memory 15 has been updated, the determination section 122 compares the first pairing information input from the memory 15 with second pairing information input from the wireless communication unit 13, and outputs a second response instruction to the registration section 123 and the response section 124 when a result of the comparison satisfies a predetermined condition.

When the second response instruction is input from the determination section 122, the registration section 123 registers identification information (for example, a MAC address) of the data collection terminal 20, which is included in the second response instruction, in the wireless communication unit 13 as a pairing partner. When the first response instruction is input from the determination section 122, the response section 124 outputs a first pairing response packet to the wireless communication unit 13. When the second response instruction is input from the determination section 122, the response section 124 outputs a second pairing response packet to the wireless communication unit 13. The upper layer communication section 121 generates an upper layer data packet from data input from the sensor unit 11, and outputs the generated upper layer data packet to the wireless communication unit 13.

The wireless communication unit 13 receives a first pairing request packet and a second pairing request packet, which are transmitted from the data collection terminal 20, and outputs a string of the received data to the storage control unit 14 and the communication control unit 12. The wireless communication unit 13 transmits the first pairing response packet, the second pairing response packet, and the upper layer data packet, which have been input from the communication control unit 12, to the data collection terminal 20 through the antenna 16. The first pairing information indicates a terminal ID of the data collection terminal 20 included in the first pairing response packet. The second pairing information indicates a terminal ID of the data collection terminal 20 included in the second pairing response packet.

The storage unit 17 stores in advance information indicating an order in which the wireless sensing terminal 10 and the data collection terminal 20 perform pairing. In the present embodiment, according to the order in which the wireless sensing terminal 10 and the data collection terminal 20 perform the pairing, first pairing is performed by exchanging the first pairing request packet and the first pairing response packet, second pairing is performed by exchanging the second pairing request packet and the second pairing response packet, and the pairing is permitted only when an out-of-body terminal ID included in the first pairing request packet coincides with an out-of-body terminal ID included in the second pairing request packet.

Figure 3:
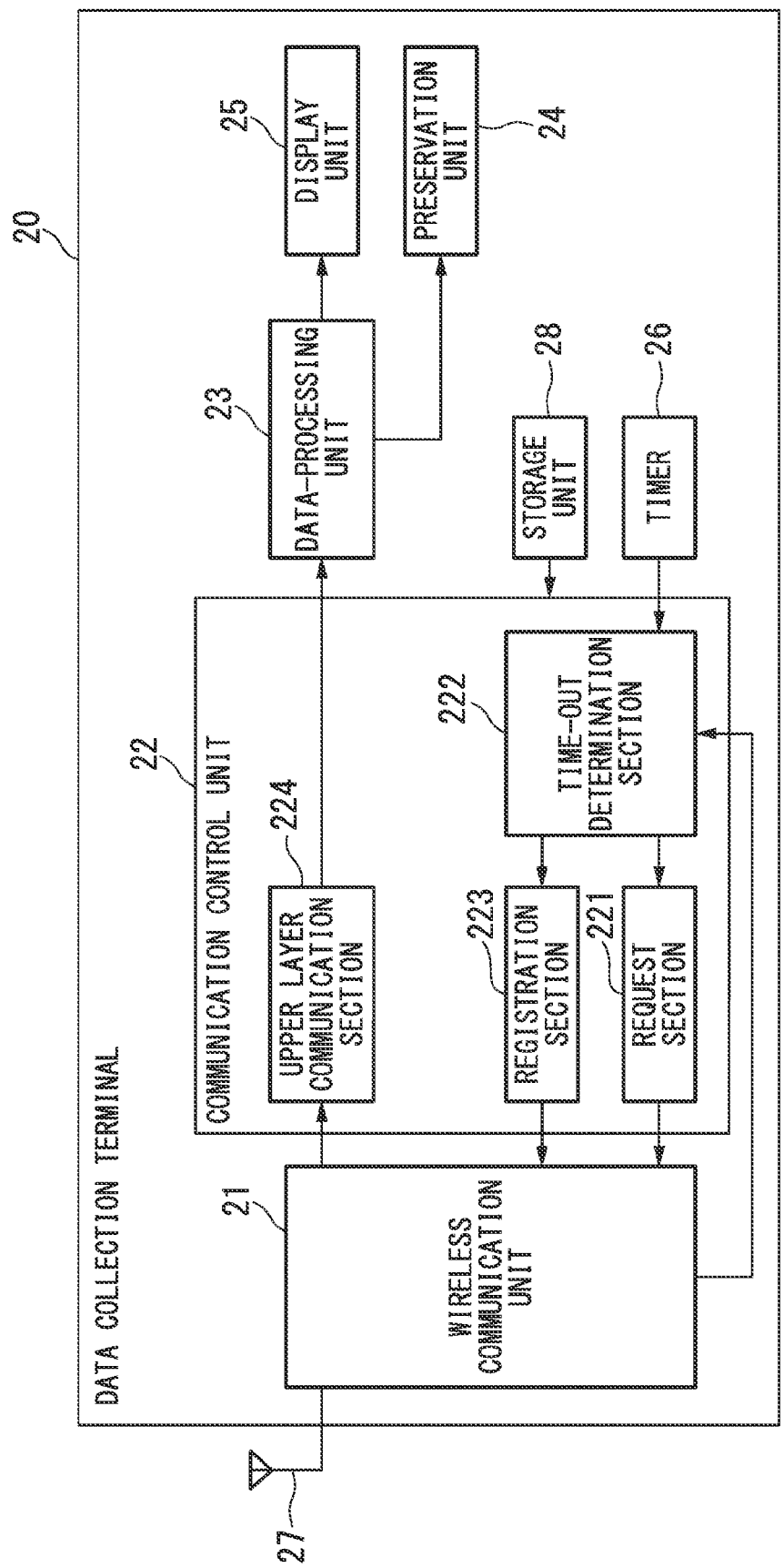
FIG. 3 is a block diagram illustrating the configuration of a data collection terminal in a first embodiment of the present invention.

Next, the configuration of the data collection terminal 20 will be described. FIG. 3 is a block diagram illustrating the configuration of the data collection terminal 20 in the present embodiment. In the illustrated example, the data collection terminal 20 includes a wireless communication unit 21, a communication control unit 22, a data-processing unit 23, a preservation unit 24, a display unit 25, a timer 26, an antenna 27, and a storage unit 28 (a storage device). The data collection terminal 20 includes a battery (not illustrated). The battery supplies power to each element provided in the data collection terminal 20.

The communication control unit 22 includes a request section 221, a time-out determination section 222, a registration section 223 (a second registration section), and an upper layer communication section 224. The request section 221 generates the first pairing request packet and the second pairing request packet, and outputs the first pairing request packet and the second pairing request packet to the wireless communication unit 21.

The time-out determination section 222 allows the timer 26 to start time counting when the wireless communication unit 21 has transmitted the first pairing request packet and the second pairing request packet. When the wireless communication unit 21 receives a second pairing packet before a preset time lapses after the timer 26 starts the time counting, the time-out determination section 222 outputs a registration instruction of the wireless sensing terminal 10, which has transmitted the second pairing packet, to the registration section 223. Meanwhile, when the wireless communication unit 21 receives no first pairing packet or second pairing packet before the preset time lapses after the timer 26 starts the time counting, the time-out determination section 222 determines time-out and regards it as pairing failure.

When the registration instruction is input from the time-out determination section 222, the registration section 223 registers identification information (for example, a MAC address) of the wireless sensing terminal 10, which is included in the registration instruction, in the wireless communication unit 21 as a pairing partner. The upper layer communication section 224 outputs an upper layer data packet, which has been input from the wireless communication unit 21, to the data-processing unit 23.

The wireless communication unit 21 transmits the first pairing request packet and the second pairing request packet, which have been input from the communication control unit 22, to the wireless sensing terminal 10 through the antenna 27. The wireless communication unit 21 receives the first pairing response packet, the second pairing response packet, and the upper layer data packet, which have been transmitted from the wireless sensing terminal 10, and outputs them to the communication control unit 22. The data-processing unit 23 converts the data, which has been acquired from the communication control unit 22, into a preservation format designated in advance, and outputs the converted data to the preservation unit 24. Furthermore, the data-processing unit 23 converts the data, which has been acquired from the communication control unit 22, into display data including text, an image and the like, and outputs the display data to the display unit 25.

The display unit 25 displays text or an image based on the display data input from the data-processing unit 23. The preservation unit 24 preserves the data input from the data-processing unit 23. The timer 26 counts time. The storage unit 28 stores in advance the same information as the information that is stored in the storage unit 17 of the wireless sensing terminal 10 and indicates the order in which the wireless sensing terminal 10 and the data collection terminal 20 perform pairing.

Next, an operation procedure between the wireless sensing terminal 10 and the data collection terminal 20 will be described.

Figure 4:
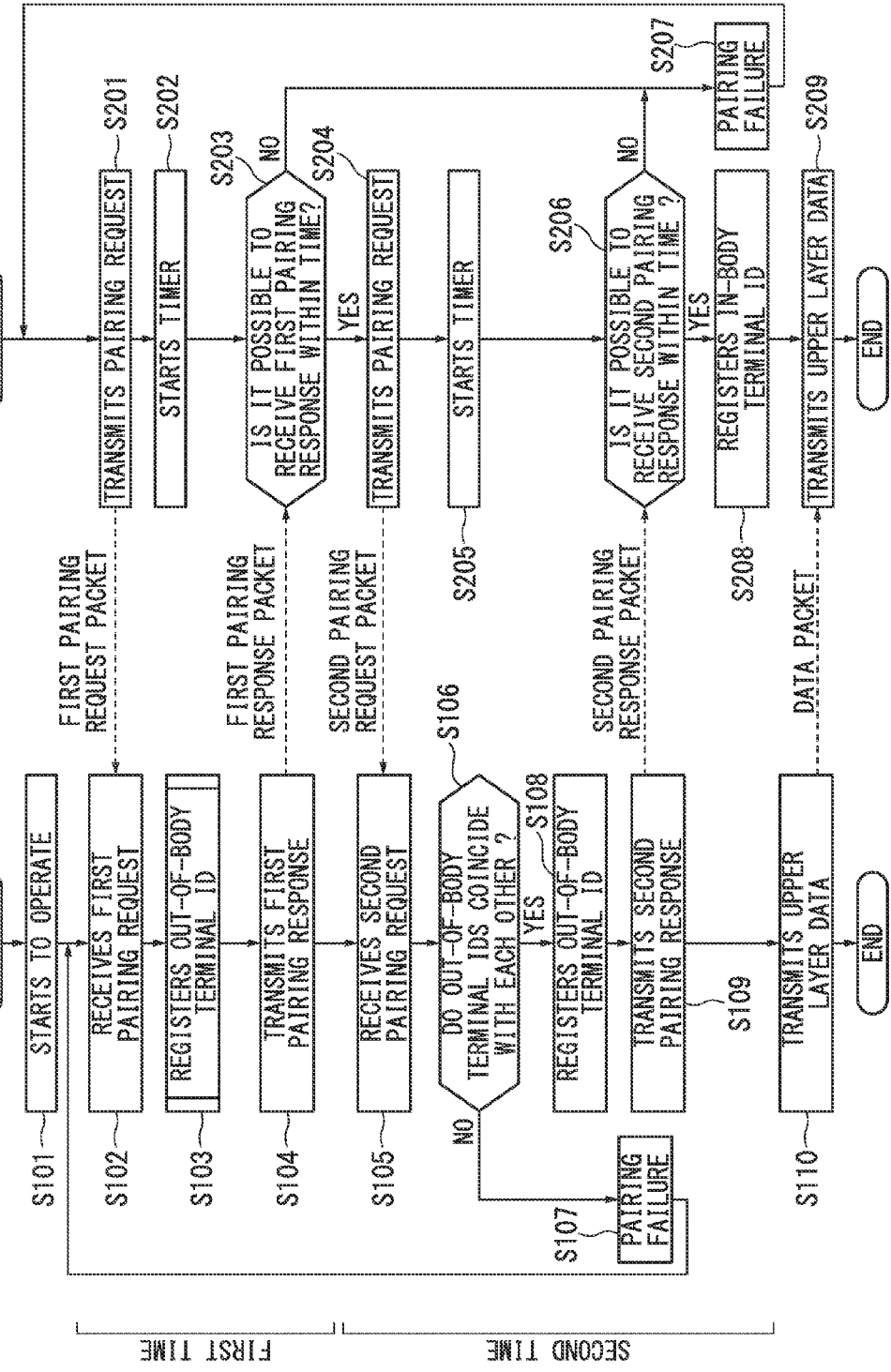
FIG. 4 is a flowchart illustrating an operation procedure between a wireless sensing terminal and a data collection terminal in a first embodiment of the present invention.

FIG. 4 is a flowchart illustrating the operation procedure between the wireless sensing terminal 10 and the data collection terminal 20 in the present embodiment.

First, the operation procedure of the wireless sensing terminal 10 will be described.

(Step S101) Each element of the wireless sensing terminal 10 starts to operate. Then, the procedure proceeds to a process of step S102.

(Step S102) The wireless communication unit 13 receives the first pairing request packet, which is transmitted from the data collection terminal 20 through a first channel, through the antenna 16. Since the wireless communication unit 13 is not able to know the first channel in advance, the wireless communication unit 13 continues a reception process until it is possible to receive the first pairing request packet while switching channels sequentially from a channel with an advanced number. Then, the procedure proceeds to a process of step S103. The process of step S102 is defined as a first pairing request reception step.

(Step S103) The storage control unit 14 stores an out-of-body terminal ID, which is included in the first pairing request packet received in the wireless communication unit 13 in the process of step S102, in the memory 105.

Then, the procedure proceeds to a process of step S104. The process of step S103 is defined as an out-of-body terminal ID storage step.

(Step S104) The response section 124 outputs the first pairing response packet to the wireless communication unit 13. The wireless communication unit 13 transmits the first pairing response packet, which has been input from the response section 124, to the data collection terminal 20 through the antenna 16. Then, the procedure proceeds to a process of step S105. The process of step S104 is defined as a first pairing response transmission step.

(Step S105) The wireless communication unit 13 receives the second pairing request packet, which is transmitted from the data collection terminal 20, through the antenna 16. Then, the procedure proceeds to a process of step S106. The process of step S105 is defined as a second pairing request reception step.

(Step S106) The determination section 122 determines whether the out-of-body terminal ID (the out-of-body terminal ID included in the first pairing request packet) stored in the memory 15 in the process of step S103 coincides with an out-of-body terminal ID included in the second pairing request packet received in the process of step S105. When the determination section 122 determines that the out-of-body terminal ID stored in the memory 15 coincides with the out-of-body terminal ID included in the second pairing request packet, the procedure proceeds to a process of step S108. Otherwise, the procedure proceeds to a process of step S107. The process of step S106 is defined as a determination step.

(Step S107) The storage control unit 14 deletes the out-of-body terminal ID stored in the memory 15 in the process of step S103. Then, the procedure returns to the process of step S102. The process of step S107 is defined as a pairing failure step.

(Step S108) The registration section 123 registers the out-of-body terminal ID, which has been determined to coincide with it in the process of step S106, in the wireless communication unit 13 as a pairing partner. Then, the procedure returns to the process of step S109. The process of step S108 is defined as an out-of-body terminal ID registration step.

(Step S109) The response section 124 outputs the second pairing response packet to the wireless communication unit 13. The wireless communication unit 13 transmits the second pairing response packet, which has been input from the response section 124, to the data collection terminal 20 through the antenna 16. Then, the procedure proceeds to a process of step S110. The process of step S109 is defined as a second pairing response transmission step.

(Step S110) The upper layer communication section 121 outputs collection data, which has been input from the sensor unit 11, to the wireless communication unit 13. The wireless communication unit 13 transmits the collection data, which has been input from the upper layer communication section 121, to the data collection terminal 20 uniquely specified by the out-of-body terminal ID registered in the process of step S108. After the transmission of the collection data is completed, the procedure ends. The process of step S110 is defined as an upper layer data communication step.

Next, the operation procedure of the data collection terminal 20 will be described.

(Step S201) The request section 221 generates the first pairing request packet and outputs the first pairing request packet to the wireless communication unit 21. The wireless communication unit 21 transmits the first pairing request packet, which has been input from the request section 221, to the wireless sensing terminal 10 through the antenna 27.

Then, the procedure proceeds to a process of step S202. The process of step S201 is defined as a first pairing request transmission step.

(Step S202) The time-out determination section 222 allows the timer 26 to start time counting when the wireless communication unit 21 has transmitted the first pairing request packet in the process of step S201. Then, the procedure proceeds to a process of step S203. The process of step S202 is defined as a first timer start step.

(Step S203) The time-out determination section 222 determines whether the wireless communication unit 21 has received the first pairing response packet before a preset time lapses after the timer 26 starts the time counting in the process of step S202. When the time-out determination section 222 determines that the wireless communication unit 21 has received the first pairing response packet before the preset time lapses after the timer 26 starts the time counting in the process of step S202, the procedure proceeds to a process of step S204. Otherwise, the procedure proceeds to a process of step S207. The process of step S203 is defined as a first time-out determination step.

(Step S204) The request section 221 generates the second pairing request packet and outputs the second pairing request packet to the wireless communication unit 21. The wireless communication unit 21 transmits the second pairing request packet, which has been input from the request section 221, to the wireless sensing terminal 10 through the antenna 27.

Then, the procedure proceeds to a process of step S205. The process of step S204 is defined as a second pairing request transmission step.

(Step S205) The time-out determination section 222 allows the timer 26 to start time counting when the wireless communication unit 21 has transmitted the second pairing request packet in the process of step S204. Then, the procedure proceeds to a process of step S206. The process of step S205 is defined as a second timer start step.

(Step S206) The time-out determination section 222 determines whether the wireless communication unit 21 has received the second pairing response packet before a preset time lapses after the timer 26 starts the time counting in the process of step S205. When the time-out determination section 222 determines that the wireless communication unit 21 has received the second pairing response packet before the preset time lapses after the timer 26 starts the time counting in the process of step S205, the procedure proceeds to a process of step S208. Otherwise, the procedure proceeds to a process of step S207. The process of step S206 is defined as a second time-out determination step.

(Step S207) The storage control unit 14 clears the time counting of the timer 26, which has started in the process of step S202 or step S206, and the procedure returns to the process of step S201. The process of step S207 is defined as a pairing failure step.

(Step S208) The registration section 223 registers an in-body terminal ID (for example, a MAC address), which is included in the second pairing response packet received in the process of step S206, in the wireless communication unit 21 as information for uniquely specifying a pairing partner. Then, the procedure proceeds to the process of step S209. The process of step S208 is defined as an in-body terminal ID registration step.

(Step S209) The wireless communication unit 21 receives the collection data, which has been transmitted from the wireless sensing terminal 10, through the antenna 27, and outputs the collection data to the upper layer communication section 224. The upper layer communication section 224 outputs the collection data, which has been input from the wireless communication unit 21, to the data-processing unit 23. After the transmission of the collection data is completed, the procedure ends. The process of step S209 is defined as an upper layer data communication step.

As described above, the storage unit 17 of the wireless sensing terminal 10 and the storage unit 28 of the data collection terminal 20 store in advance the information indicating the order in which the wireless sensing terminal 10 and the data collection terminal 20 perform the pairing. In the present embodiment, according to the order in which the wireless sensing terminal 10 and the data collection terminal 20 perform the pairing, the first pairing is performed by exchanging the first pairing request packet and the first pairing response packet, the second pairing is performed by exchanging the second pairing request packet and the second pairing response packet, and the pairing is permitted only when the out-of-body terminal ID included in the first pairing request packet coincides with the out-of-body terminal ID included in the second pairing request packet.

Consequently, since the data collection terminal 20, which does not store the same information as the information stored in advance in the storage unit 17 of the wireless sensing terminal 10 and indicates the order in which the pairing is performed, does not know the order in which the pairing is performed, the data collection terminal 20 is not able to communicate with the wireless sensing terminal 10. Similarly, since the wireless sensing terminal 10, which does not store the same information as the information stored in advance in the storage unit 28 of the data collection terminal 20 and indicates the order in which the pairing is performed, does not know the order in which the pairing is performed, the wireless sensing terminal 10 is not able to communicate with the data collection terminal 20. In this way, there is no change in a hardware configuration that increases battery consumption, so that it is possible to reduce the possibility of a fraudulent connection.

In the aforementioned embodiment, according to the order in which the pairing is performed, the first pairing is performed by exchanging the first pairing request packet and the first pairing response packet, the second pairing is performed by exchanging the second pairing request packet and the second pairing response packet, and the pairing is permitted only when the out-of-body terminal ID included in the first pairing request packet coincides with the out-of-body terminal ID included in the second pairing request packet. However, the present invention is not limited thereto. For example, third pairing may be further performed by exchanging a third pairing request packet and a third pairing response packet, and the pairing may be permitted only when the out-of-body terminal ID included in the first pairing request packet, the out-of-body terminal ID included in the second pairing request packet, and an out-of-body terminal ID included in the third pairing request packet coincide with one another. Moreover, the pairing request packet and the pairing response packet may also be exchanged four or more times. The pairing may be permitted not only when all the out-of-body terminal IDs coincide with one another, but also when some of the out-of-body terminal IDs coincide with one another.

In the aforementioned embodiment, the first pairing request packet and the second pairing request packet include the out-of-body terminal IDs, respectively. However, the present invention is not limited thereto. For example, the second pairing request packet may include information decided in advance other than the out-of-body terminal ID, and when the information decided in advance is included in the second pairing request packet, the pairing may also be permitted. For example, the second pairing request packet may include a result obtained by applying a conversion formula (for example, the out-of-body terminal ID+α) decided in advance to the out-of-body terminal ID, may include the in-body terminal ID, or may include a result obtained by applying a conversion formula (for example, the out-of-body terminal ID+the in-body terminal ID) decided in advance to the out-of-body terminal ID and the in-body terminal ID.

(Second Embodiment)

Hereinafter, a second embodiment of the present invention will be described with reference to the accompanying drawings. A biological data-monitoring system in the present embodiment includes a wireless sensing terminal and a data collection terminal, similarly to the first embodiment. The difference between the present embodiment and the first embodiment is the configuration of a communication control unit provided in the wireless sensing terminal and the configuration of a communication control unit provided in the data collection terminal.

Figure 5:
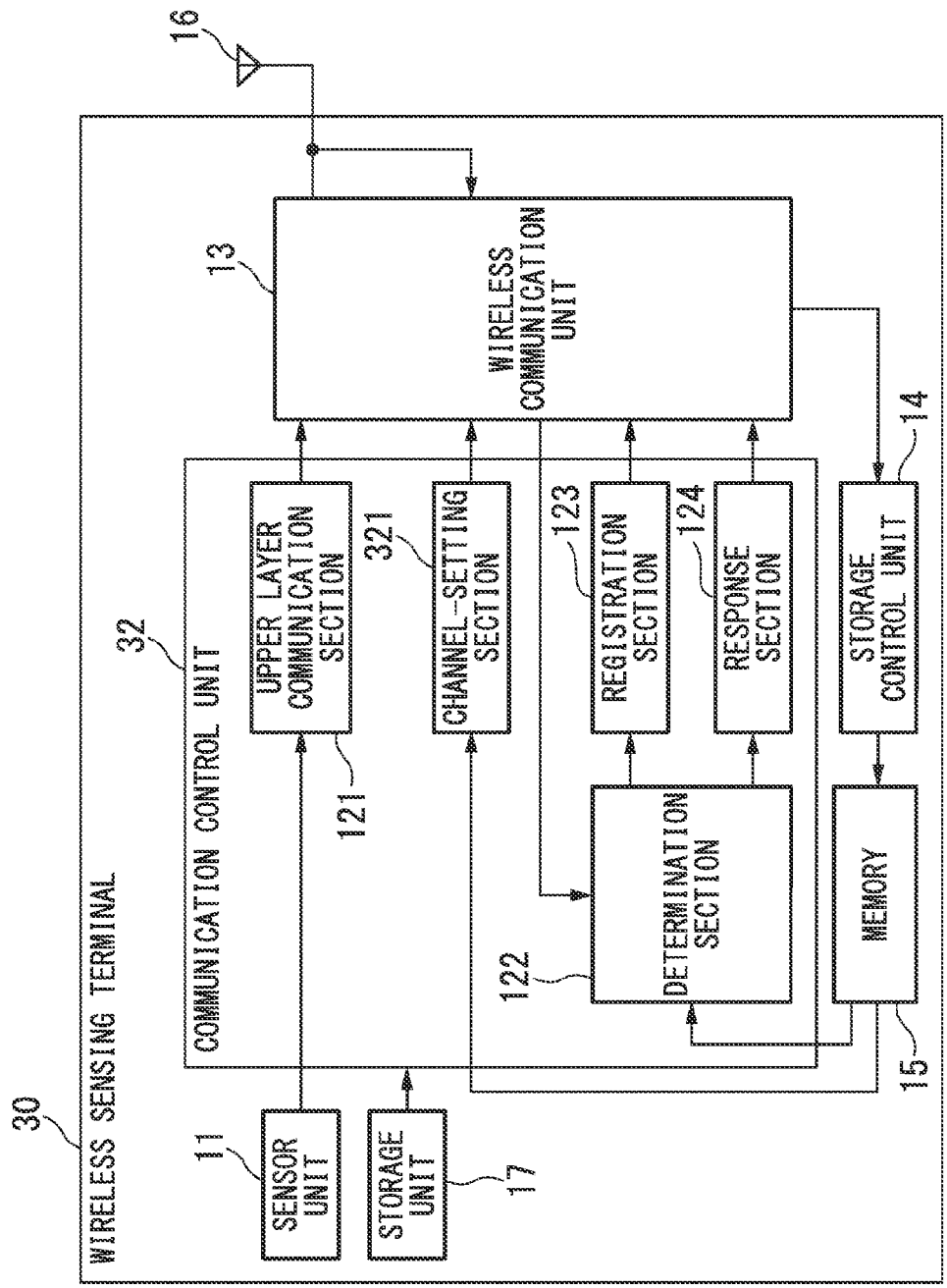
FIG. 5 is a block diagram illustrating the configuration of a wireless sensing terminal in a second embodiment of the present invention.

Next, the configuration of the wireless sensing terminal will be described. FIG. 5 is a block diagram illustrating the configuration of a wireless sensing terminal 30 in the present embodiment. In the illustrated example, the wireless sensing terminal 30 includes a sensor unit 11, a communication control unit 32, a wireless communication unit 13, a storage control unit 14, a memory 15, an antenna 16, and a storage unit 17. The wireless sensing terminal 30 includes a battery (not illustrated). The battery supplies power to each element provided in the wireless sensing terminal 30.

The sensor unit 11, the wireless communication unit 13, the storage control unit 14, the memory 15, the antenna 16, and the storage unit 17 are the same as the elements in the first embodiment. The communication control unit 32 includes an upper layer communication section 121, a determination section 122, a registration section 123, a response section 124, and a channel-setting section 321, and controls the wireless communication unit 13. The upper layer communication section 121, the determination section 122, the registration section 123, and the response section 124 are the same as the elements in the first embodiment.

The channel-setting section 321 starts to operate, and for example, switches a channel of the wireless communication unit 13 to a first channel CH_A, through which a first pairing request packet is transmitted, while changing channels sequentially from a channel with an advanced number. The channel-setting section 321 switches the channel of the wireless communication unit 13 to a second channel CH_B, through which a second pairing request packet is transmitted, after the wireless communication unit 13 transmits a first pairing response packet.

Figure 6:
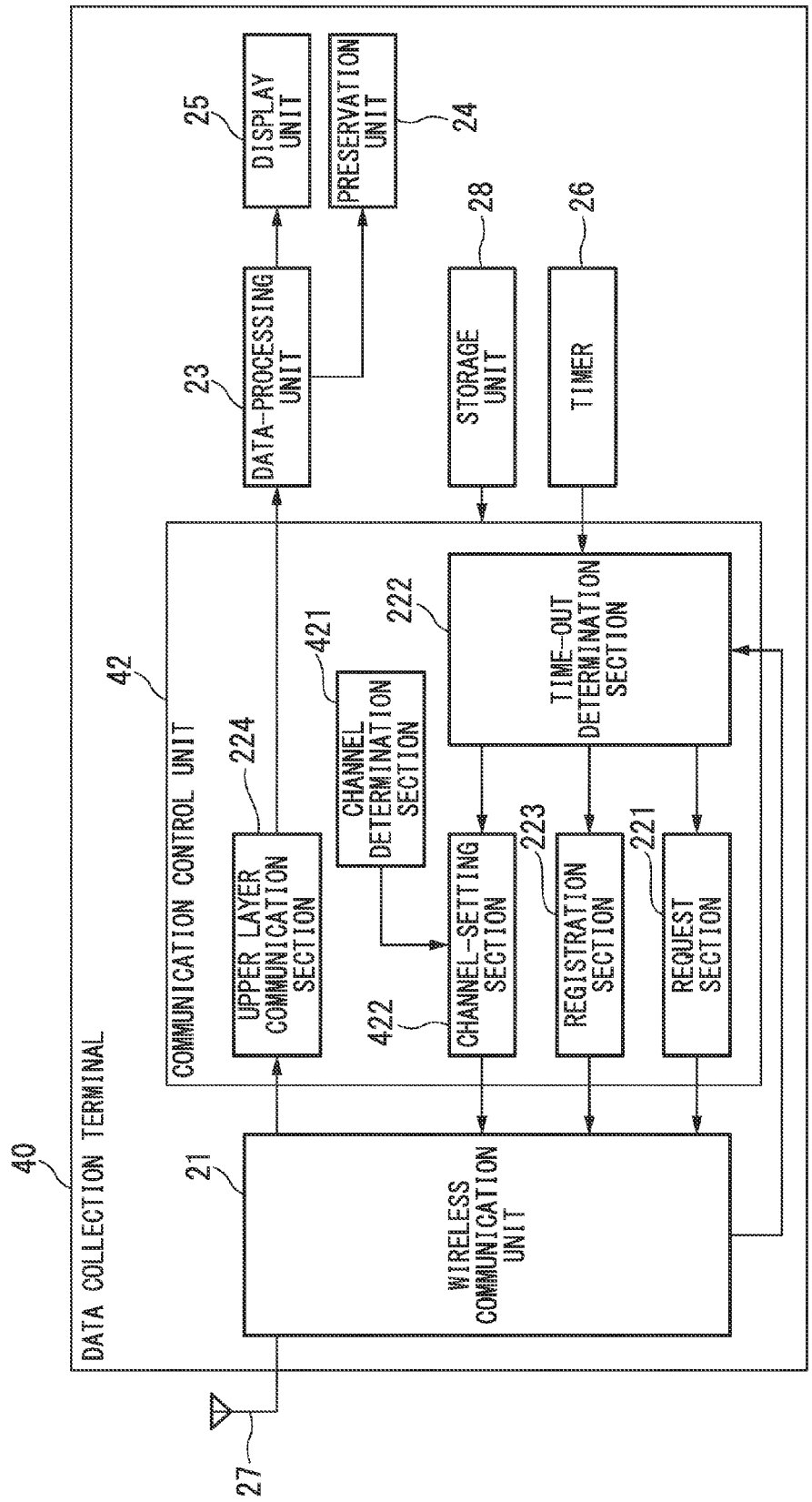
FIG. 6 is a block diagram illustrating the configuration of a data collection terminal in a second embodiment of the present invention.

Next, the configuration of the data collection terminal 40 will be described. FIG. 6 is a block diagram illustrating the configuration of the data collection terminal 40 in the present embodiment. In the illustrated example, the data collection terminal 40 includes a wireless communication unit 21, a communication control unit 42, a data-processing unit 23, a preservation unit 24, a display unit 25, a timer 26, an antenna 27, and a storage unit 28. The data collection terminal 40 includes a battery (not illustrated). The battery supplies power to each element provided in the data collection terminal 40.

The wireless communication unit 21, the data-processing unit 23, the preservation unit 24, the display unit 25, the timer 26, the antenna 27, and the storage unit 28 provided in the data collection terminal 40 are the same as the elements in the first embodiment. The communication control unit 42 includes a request section 221, a time-out determination section 222, a registration section 223, an upper layer communication section 224, a channel decision section 421, and a channel-setting section 422. The request section 221, the time-out determination section 222, the registration section 223, and the upper layer communication section 224 are the same as the elements in the first embodiment.

The channel decision section 421 decides a first channel that is used for the transmission of the first paring request packet and a second channel that is used for the transmission of the second paring request packet from all channels, and outputs channel information indicating the decided channels to the channel-setting section 422. According to a method by which the channel decision section 421 decides the channels, for example, two channels may be selected by carrier sensing sequentially from channels with a low interference reception level, or in the state in which a threshold value has been set in advance, two channels may be arbitrarily selected from channels with an interference reception level equal to or less than the threshold value.

The channel-setting section 422 starts to operate and sets a communication channel of the wireless communication unit 21 to the first channel. The channel-setting section 422 switches the communication channel of the wireless communication unit 21 to the second channel when a channel change instruction is input from the determination section 122. After the communication channel of the wireless communication unit 21 is set to the first channel, the request section 221 generates the first pairing request packet and outputs the first pairing request packet to the wireless communication unit 21. After the communication channel of the wireless communication unit 21 is set to the second channel, the request section 221 generates the second pairing request packet and outputs the second pairing request packet to the wireless communication unit 21.

Next, an operation procedure between the wireless sensing terminal 30 and the data collection terminal 40 will be described.

Figure 7:
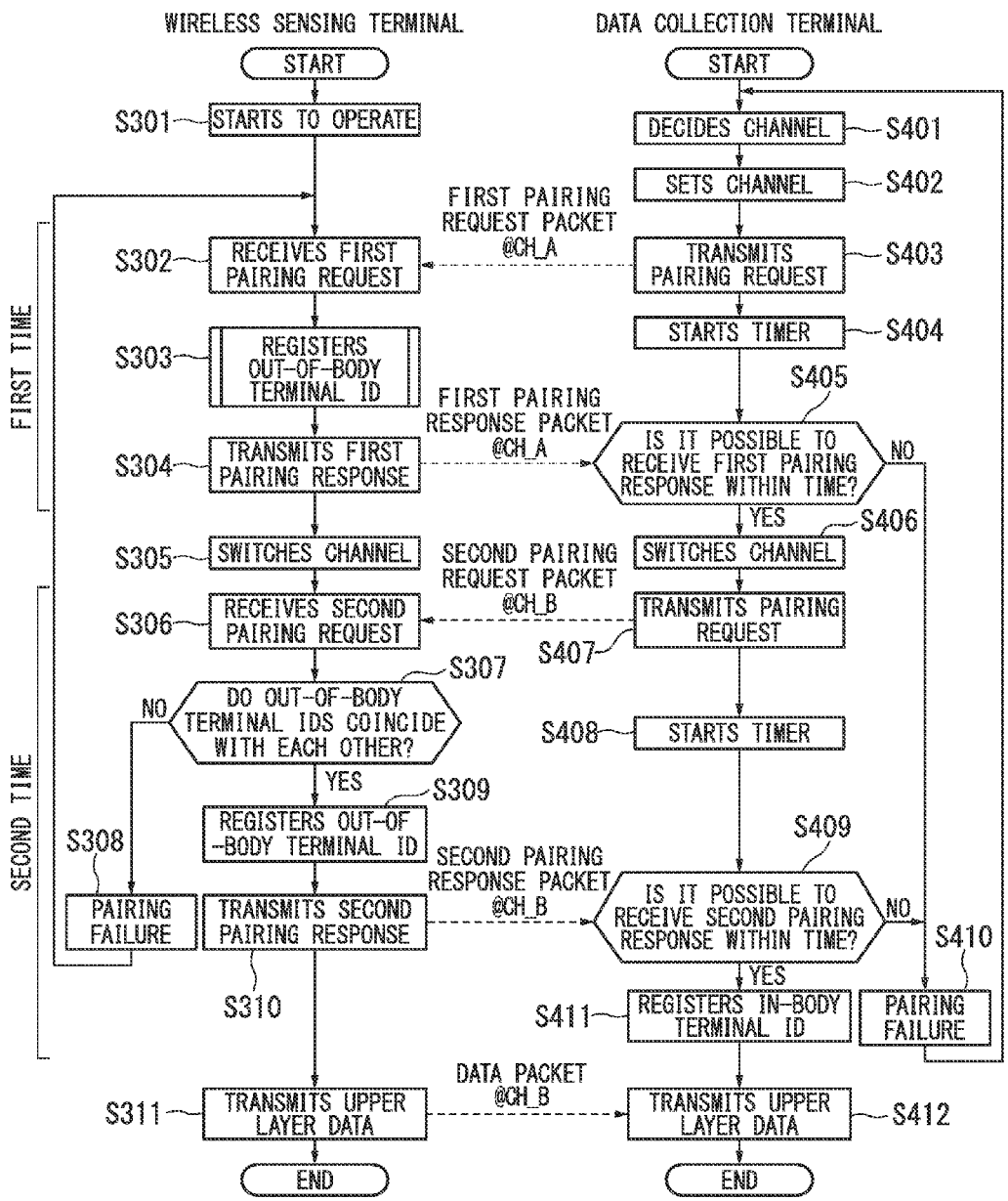
FIG. 7 is a flowchart illustrating an operation procedure between a wireless sensing terminal and a data collection terminal in a second embodiment of the present invention.

FIG. 7 is a flowchart illustrating the operation procedure between the wireless sensing terminal 30 and the data collection terminal 40 in the present embodiment.

First, the operation procedure of the wireless sensing terminal 30 will be described.

Processes of step S301 and step S302 are the same as those of step S101 and step S102 in the first embodiment.

(Step S303) The storage control unit 14 stores, in the memory 105, an out-of-body terminal ID, which is included in the first pairing request packet received in the wireless communication unit 13 in the process of step S302, and second channel information. Then, the procedure proceeds to a process of step S304. The process of step S303 is defined as an out-of-body terminal ID storage step.

(Step S304) The response section 124 outputs the first pairing response packet to the wireless communication unit 13. The wireless communication unit 13 transmits the first pairing response packet, which has been input from the response section 124, to the data collection terminal 40, through the antenna 16. Then, the procedure proceeds to a process of step S305. The process of step S304 is defined as a first pairing response transmission step.

(Step S305) The channel-setting section 321 reads the second channel information stored in the memory 15 in the process of step S303, and switches the communication channel of the wireless communication unit 21 to the second channel. Then, the procedure proceeds to a process of step S306. The process of step S305 is defined as a channel-switching step.

(Step S306) The wireless communication unit 13 receives the second pairing request packet, which is transmitted from the data collection terminal 40, through the antenna 16 using the second channel set in the process of step S305. Then, the procedure proceeds to a process of step S307. The process of step S306 is defined as a second pairing request reception step.

(Step S307) The determination section 122 determines whether the out-of-body terminal ID (the out-of-body terminal ID included in the first pairing request packet) stored in the memory 15 in the process of step S303 coincides with an out-of-body terminal ID included in the second pairing request packet received in the process of step S306. When the determination section 122 determines that the out-of-body terminal ID stored in the memory 15 coincides with the out-of-body terminal ID included in the second pairing request packet, the procedure proceeds to a process of step S309. Otherwise, the procedure proceeds to a process of step S308. The process of step S307 is defined as a determination step.

(Step S308) The storage control unit 14 deletes the out-of-body terminal ID stored in the memory 15 in the process of step S303. Then, the procedure returns to the process of step S302. The process of step S308 is defined as a pairing failure step.

(Step S309) The registration section 123 registers the out-of-body terminal ID, which has been determined to coincide with it in the process of step S307, in the wireless communication unit 13 as a pairing partner. Then, the procedure returns to the process of step S310. The process of step S309 is defined as an out-of-body terminal ID registration step.

(Step S310) The response section 124 outputs the second pairing response packet to the wireless communication unit 13. The wireless communication unit 13 transmits the second pairing response packet, which has been input from the response section 124, to the data collection terminal 40 through the antenna 16 using the second channel set in the process of step S305. Then, the procedure proceeds to a process of step S311. The process of step S310 is defined as a second pairing response transmission step.

(Step S311) The upper layer communication section 121 outputs collection data, which has been input from the sensor unit 11, to the wireless communication unit 13. The wireless communication unit 13 transmits the collection data, which has been input from the upper layer communication section 121, to the data collection terminal 40, which is uniquely specified by the out-of-body terminal ID registered in the process of step S309, using the second channel set in the process of step S305. After the transmission of the collection data is completed, the procedure ends. The process of step S311 is defined as an upper layer data communication step.

Next, the operation procedure of the data collection terminal 40 will be described.

(Step S401) The channel decision section 421 decides the first channel that is used for the transmission of the first paring request packet and the second channel that is used for the transmission of the second paring request packet from all channels, and outputs channel information indicating the decided channels to the channel-setting section 422. Then, the procedure proceeds to a process of step S402. The process of step S401 is defined as a channel decision step.

(Step S402) The channel-setting section 422 sets the communication channel of the wireless communication unit 21 to the first channel based on the channel information input in the process of step S401. Then, the procedure proceeds to a process of step S403. The process of step S402 is defined as a channel-setting step.

(Step S403) The request section 221 generates the first pairing request packet and outputs the first pairing request packet to the wireless communication unit 21. The wireless communication unit 21 transmits the first pairing request packet, which has been input from the request section 221, to the wireless sensing terminal 30 through the antenna 27 using the first channel set in the process of step S402. Then, the procedure proceeds to a process of step S404. The process of step S403 is defined as a first pairing request transmission step.

(Step S404) The time-out determination section 222 allows the timer 26 to start time counting when the wireless communication unit 21 has transmitted the first pairing request packet in the process of step S403. Then, the procedure proceeds to a process of step S405. The process of step S404 is defined as a first timer start step.

(Step S405) The time-out determination section 222 determines whether the wireless communication unit 21 has received the first pairing response packet before a preset time lapses after the timer 26 starts the time counting in the process of step S404. When the time-out determination section 222 determines that the wireless communication unit 21 has received the first pairing response packet before the preset time lapses after the timer 26 starts the time counting in the process of step S404, the procedure proceeds to a process of step S406. Otherwise, the procedure proceeds to a process of step S410. The process of step S405 is defined as a first time-out determination step.

(Step S406) The channel-setting section 422 sets the communication channel of the wireless communication unit 21 to the second channel based on the channel information input in the process of step S401. Then, the procedure proceeds to a process of step S407. The process of step S406 is defined as a channel-switching step.

(Step S407) The request section 221 generates the second pairing request packet and outputs the second pairing request packet to the wireless communication unit 21. The wireless communication unit 21 transmits the second pairing request packet, which has been input from the request section 221, to the wireless sensing terminal 30 through the antenna 27 using the second channel set in the process of step S406. Then, the procedure proceeds to a process of step S408. The process of step S407 is defined as a second pairing request transmission step.

(Step S408) The time-out determination section 222 allows the timer 26 to start time counting when the wireless communication unit 21 has transmitted the second pairing request packet in the process of step S407. Then, the procedure proceeds to a process of step S409. The process of step S408 is defined as a second timer start step.

(Step S409) The time-out determination section 222 determines whether the wireless communication unit 21 has received the second pairing response packet before a preset time lapses after the timer 26 starts the time counting in the process of step S408. When the time-out determination section 222 determines that the wireless communication unit 21 has received the second pairing response packet before the preset time lapses after the timer 26 starts the time counting in the process of step S408, the procedure proceeds to a process of step S411. Otherwise, the procedure proceeds to a process of step S410. The process of step S409 is defined as a second time-out determination step.

(Step S410) The storage control unit 14 clears the time counting of the timer 26, which has started in the process of step S404 or step S408, and the procedure returns to the process of step S401. The process of step S410 is defined as a pairing failure step.

(Step S411) The registration section 223 registers an in-body terminal ID (for example, a MAC address), which is included in the second pairing response packet received in the process of step S409, in the wireless communication unit 21 as information for uniquely specifying a pairing partner. Then, the procedure proceeds to the process of step S412. The process of step S411 is defined as an in-body terminal ID registration step.

(Step S412) The wireless communication unit 21 receives the collection data, which has been transmitted from the wireless sensing terminal 30, through the antenna 27 using the second channel set in the process of step S406, and outputs the collection data to the upper layer communication section 224. The upper layer communication section 224 outputs the collection data, which has been input from the wireless communication unit 21, to the data-processing unit 23. After the transmission of the collection data is completed, the procedure ends. The process of step S412 is defined as an upper layer data communication step.

As described above, the storage unit 17 of the wireless sensing terminal 30 and the storage unit 28 of the data collection terminal 40 store in advance the information indicating the order in which the wireless sensing terminal 30 and the data collection terminal 40 perform the pairing. In the present embodiment, according to the order in which the wireless sensing terminal 30 and the data collection terminal 40 perform the pairing, the first pairing is performed using the first channel, the second pairing is performed using the second channel, and the pairing is permitted only when the out-of-body terminal ID included in the first pairing request packet coincides with the out-of-body terminal ID included in the second pairing request packet.

Consequently, since the data collection terminal 40, which does not store the same information as the information stored in advance in the storage unit 17 of the wireless sensing terminal 30 and indicates the order in which the pairing is performed, does not know the order in which the pairing is performed, the data collection terminal 40 is not able to communicate with the wireless sensing terminal 30. Similarly, since the wireless sensing terminal 30, which does not store the same information as the information stored in advance in the storage unit 28 of the data collection terminal 40 and indicates the order in which the pairing is performed, does not know the order in which the pairing is performed, the wireless sensing terminal 30 is not able to communicate with the data collection terminal 40. In this way, there is no change in a hardware configuration that increases battery consumption, so that it is possible to reduce the possibility of a fraudulent connection.

In the present embodiment, the first pairing and the second pairing are performed using different channels from each other. Consequently, since time and effort are required in fraudulent data analysis by a third party, it is possible to further reduce the possibility of a fraudulent connection.

(Third Embodiment)

Hereinafter, a third embodiment of the present invention will be described with reference to the accompanying drawings. A biological data-monitoring system in the present embodiment includes a wireless sensing terminal and a data collection terminal, similarly to the second embodiment. The difference between the present embodiment and the second embodiment is that the wireless sensing terminal of the present embodiment includes a timer.

Figure 8:
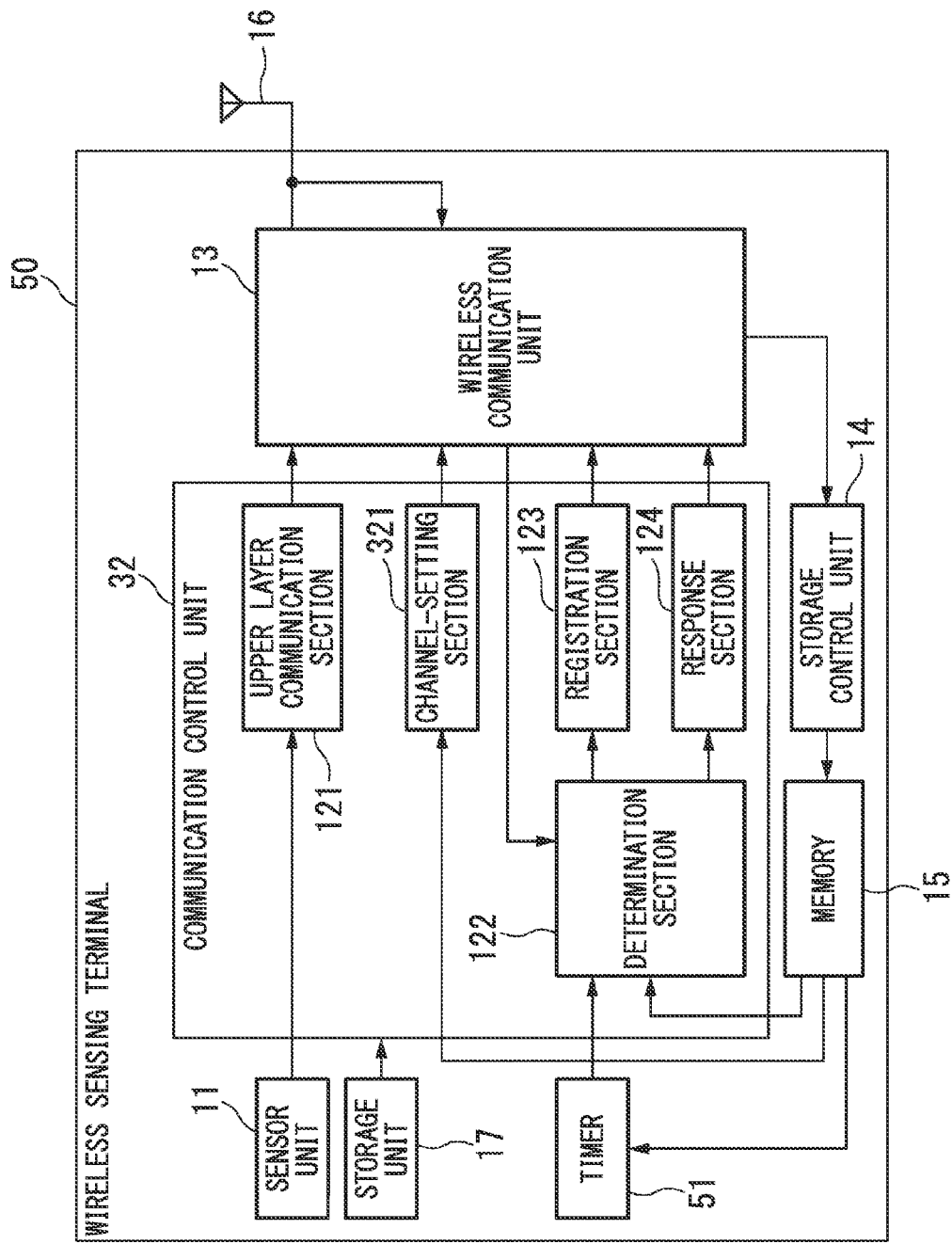
FIG. 8 is a block diagram illustrating the configuration of a wireless sensing terminal in a third embodiment of the present invention.

Next, the configuration of the wireless sensing terminal will be described. FIG. 8 is a block diagram illustrating the configuration of a wireless sensing terminal 50 in the present embodiment. In the illustrated example, the wireless sensing terminal 50 includes a sensor unit 11, a communication control unit 32, a wireless communication unit 13, a storage control unit 14, a memory 15, an antenna 16, a storage unit 17, and a timer 51. The wireless sensing terminal 50 includes a battery (not illustrated). The battery supplies power to each element provided in the wireless sensing terminal 50.

The sensor unit 11, the communication control unit 32, the wireless communication unit 13, the storage control unit 14, the memory 15, the antenna 16, and the storage unit 17 are the same as the elements in the second embodiment. The timer 51 counts time. In detail, the timer 51 monitors the memory 15, and starts (starts the timer) the counting of time when first pairing information is written in the memory 15. A determination section 122 confirms a passage time (counted time) of the timer 51 when the wireless communication unit 13 has received a second pairing request packet, determines whether the passage time is within a prescribed time, and determines pairing failure when the passage time is equal to or more than the prescribed time, as well as determination regarding whether out-of-body terminal IDs coincide with each other.

Next, the configuration of the data collection terminal 40 will be described. The data collection terminal 40 in the present embodiment is the same as the data collection terminal 40 in the second embodiment.

Next, an operation procedure between the wireless sensing terminal 50 and the data collection terminal 40 will be described.

Figure 9:
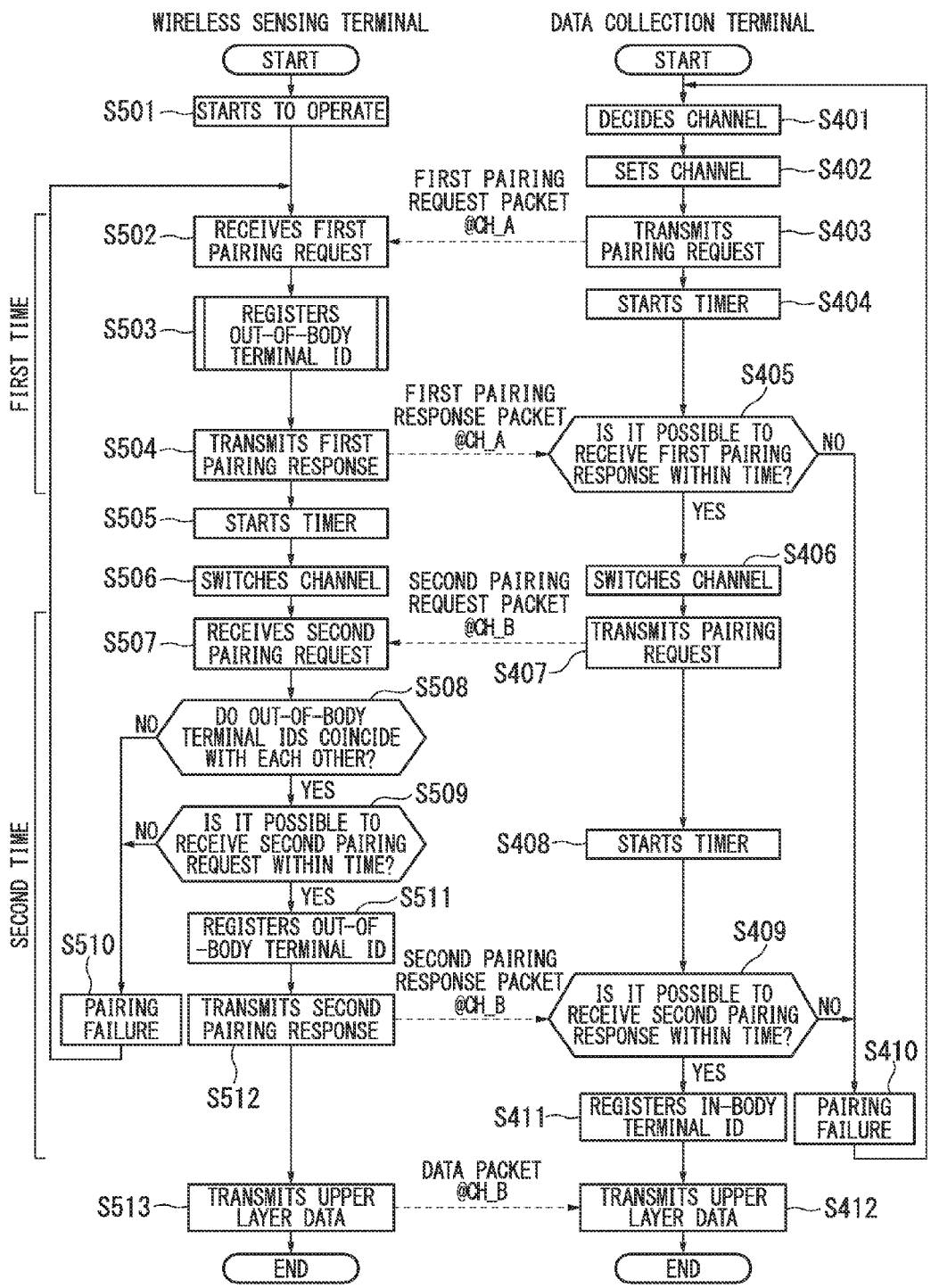
FIG. 9 is a flowchart illustrating an operation procedure between a wireless sensing terminal and a data collection terminal in a third embodiment of the present invention.

FIG. 9 is a flowchart illustrating the operation procedure between the wireless sensing terminal 50 and the data collection terminal 40 in the present embodiment.

First, the operation procedure of the wireless sensing terminal 50 will be described.

Processes of step S501 to step S504 are the same as those of step S301 to step S304 in the second embodiment.

(Step S505) The timer 51 starts time counting when the memory 15 has stored an out-of-body terminal ID in the process of S503. Then, the procedure proceeds to a process of step S506. The process of step S505 is defined as a timer start step.

Processes of step S506 to step S508 are the same as those of step S305 to step S307 in the second embodiment.

(Step S509) The determination section 122 determines whether the wireless communication unit 13 has received a second pairing request packet before a preset time lapses after the timer 51 starts the time counting in the process of step S505. When the determination section 122 determines that the wireless communication unit 13 has received the second pairing request packet before the preset time lapses after the timer 51 starts the time counting in the process of step S505, the procedure proceeds to a process of step S511. Otherwise, the procedure proceeds to a process of step S510. The process of step S509 is defined as a time-out determination step.

Processes of step S510 to step S513 are the same as those of step S309 to step S311 in the second embodiment.

Next, the operation procedure of the data collection terminal 40 will be described. The operation procedure of the data collection terminal 40 in the present embodiment is the same as the operation procedure of the data collection terminal 40 in the second embodiment.

As described above, in the present embodiment, the wireless sensing terminal 50 permits no pairing when it is not possible to receive the second pairing request packet within a predetermined time after the first pairing response packet is transmitted. Consequently, time is required in fraudulent data analysis by a third party, and when it is not possible to transmit the second pairing request packet within the predetermined time, no pairing is permitted, so that it is possible to further reduce the possibility of a fraudulent connection.

(Fourth Embodiment)

Hereinafter, a fourth embodiment of the present invention will be described with reference to the accompanying drawings. A biological data-monitoring system in the present embodiment includes a wireless sensing terminal and a data collection terminal, similarly to the second embodiment. The difference between the present embodiment and the second embodiment is that the wireless sensing terminal of the present embodiment includes a candidate storage unit.

Figure 10:
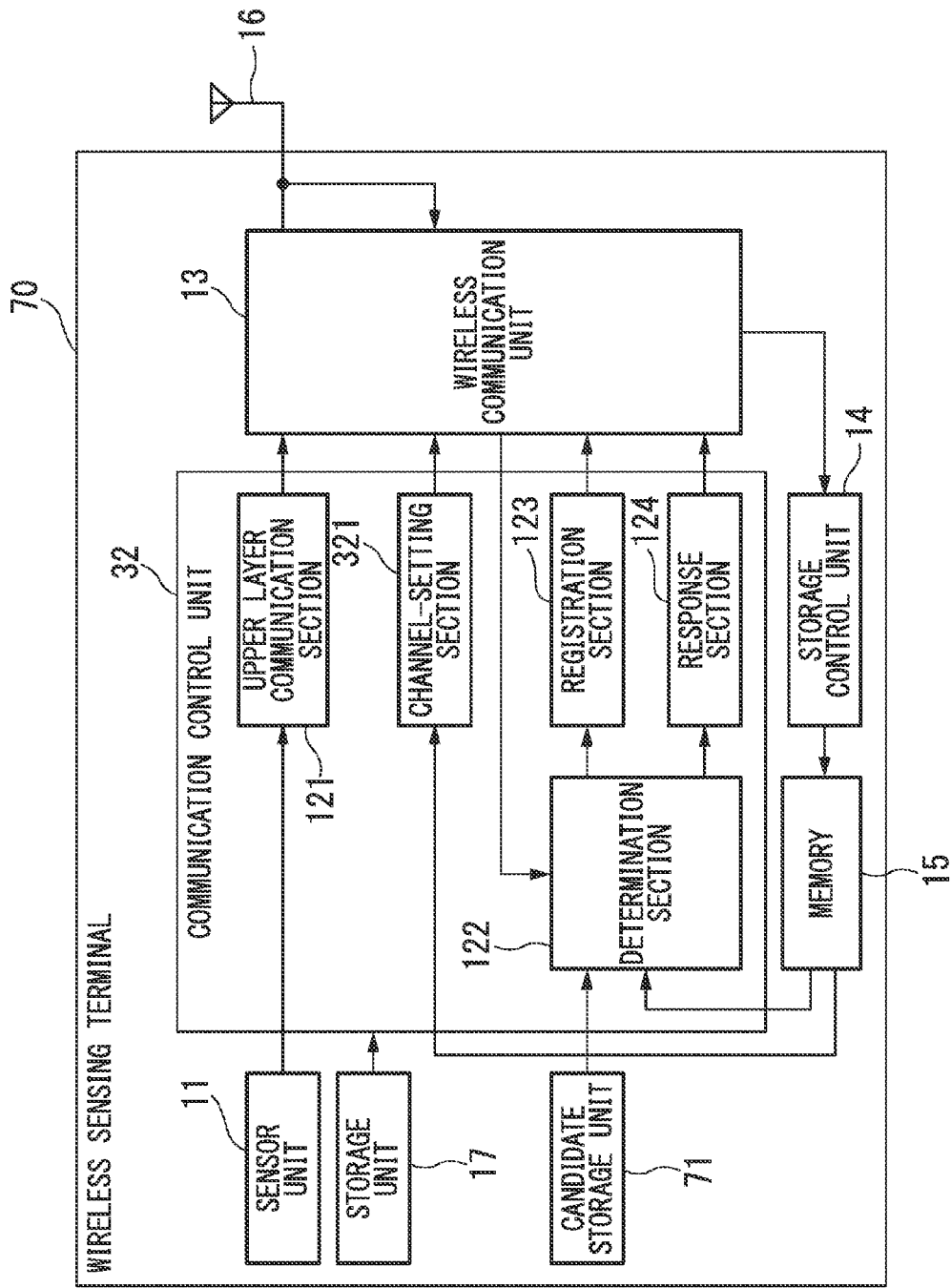
FIG. 10 is a block diagram illustrating the configuration of a wireless sensing terminal in a fourth embodiment of the present invention.

Next, the configuration of the wireless sensing terminal will be described. FIG. 10 is a block diagram illustrating the configuration of a wireless sensing terminal 70 in the present embodiment. In the illustrated example, the wireless sensing terminal 70 includes a sensor unit 11, a communication control unit 32, a wireless communication unit 13, a storage control unit 14, a memory 15, an antenna 16, a storage unit 17, and a candidate storage unit 71. The wireless sensing terminal 70 includes a battery (not illustrated). The battery supplies power to each element provided in the wireless sensing terminal 70.

The sensor unit 11, the communication control unit 32, the wireless communication unit 13, the storage control unit 14, the memory 15, the antenna 16, and the storage unit 17 are the same as the elements in the second embodiment. The candidate storage unit 71 stores in advance a list of one or more out-of-body terminal IDs of out-of-body terminals to be paired. The determination section 122 determines whether an out-of-body terminal ID of the data collection terminal 40, which is included in first pairing information, is included in the list of the out-of-body terminal IDs of out-of-body terminals to be paired, which is stored in the candidate storage unit 71, and determines pairing failure when the out-of-body terminal ID of the data collection terminal 40 is not included in the list.

Next, the configuration of the data collection terminal 40 will be described. The data collection terminal 40 in the present embodiment is the same as the data collection terminal 40 in the second embodiment.

Next, an operation procedure between the wireless sensing terminal 70 and the data collection terminal 40 will be described.

Figure 11:
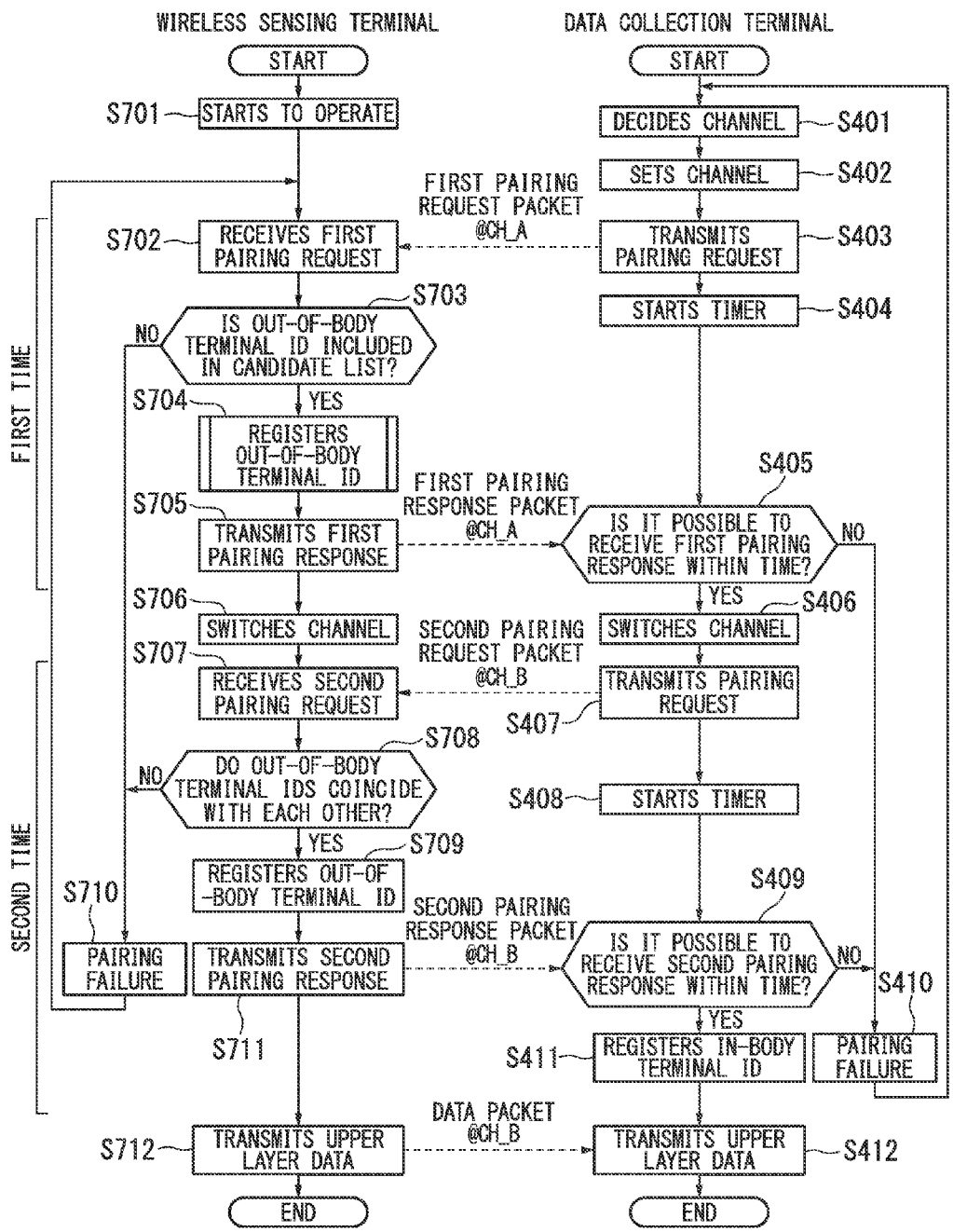
FIG. 11 is a flowchart illustrating an operation procedure between a wireless sensing terminal and a data collection terminal in a fourth embodiment of the present invention.

FIG. 11 is a flowchart illustrating the operation procedure between the wireless sensing terminal 70 and the data collection terminal 40 in the present embodiment.

First, the operation procedure of the wireless sensing terminal 70 will be described.

Processes of step S701 and step S702 are the same as those of step S301 and step S302 in the second embodiment.

(Step S703) The determination section 122 determines whether an out-of-body terminal ID, which is included in first pairing request packet received in the process of step S702, is included in the list of the out-of-body terminal IDs of out-of-body terminals to be paired, which is stored in the candidate storage unit 71. When the determination section 122 determines that the out-of-body terminal ID, which is included in first pairing request packet received in the process of step S702, is included in the list of the out-of-body terminal IDs of out-of-body terminals to be paired, which is stored in the candidate storage unit 71, the procedure proceeds to a process of step S704. Otherwise, the procedure proceeds to a process of step S710. The process of step S703 is defined as an out-of-body terminal ID check step.

Processes of step S704 to step S712 are the same as those of step S303 to step S311 in the second embodiment.

Next, the operation procedure of the data collection terminal 40 will be described. The operation procedure of the data collection terminal 40 in the present embodiment is the same as the operation procedure of the data collection terminal 40 in the second embodiment.

As described above, in the present embodiment, the wireless sensing terminal 70 permits no pairing when an out-of-body terminal ID included in the received first pairing request packet is not included in the list of out-of-body terminal IDs stored in advance. Consequently, it is possible to further reduce the possibility of a fraudulent connection.

(Fifth Embodiment)

Hereinafter, a fifth embodiment of the present invention will be described with reference to the accompanying drawings. A biological data-monitoring system in the present embodiment includes a wireless sensing terminal and a data collection terminal, similarly to the second embodiment. The difference between the present embodiment and the second embodiment is that the wireless sensing terminal and the data collection terminal of the present embodiment each includes a common information storage unit.

Figure 12:
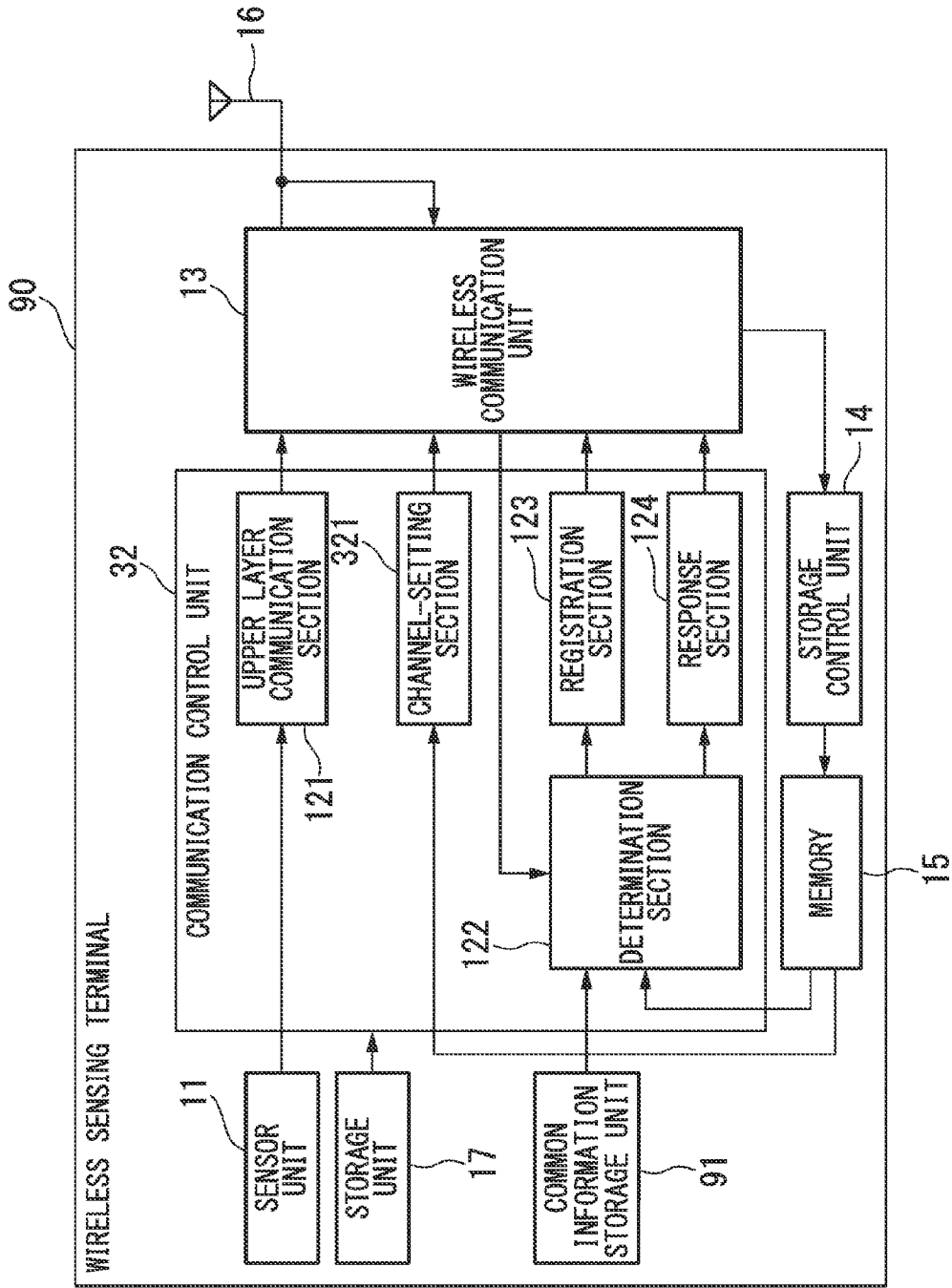
FIG. 12 is a block diagram illustrating the configuration of a wireless sensing terminal in a fifth embodiment of the present invention.

Next, the configuration of the wireless sensing terminal will be described. FIG. 12 is a block diagram illustrating the configuration of a wireless sensing terminal 90 in the present embodiment. In the illustrated example, the wireless sensing terminal 90 includes a sensor unit 11, a communication control unit 32, a wireless communication unit 13, a storage control unit 14, a memory 15, an antenna 16, a storage unit 17, and a common information storage unit 91. The wireless sensing terminal 90 includes a battery (not illustrated). The battery supplies power to each element provided in the wireless sensing terminal 90.

The sensor unit 11, the communication control unit 32, the wireless communication unit 13, the storage control unit 14, the memory 15, the antenna 16, and the storage unit 17 are the same as the elements in the second embodiment. The common information storage unit 91 stores first common information decided in advance and second common information decided in advance. The first common information and the second common information may be any information. For example, the first common information and the second common information may be arbitrary bit sequences or a part of parameters of wireless communication such as a beacon transmission interval. The determination section 122 determines whether the first common information is included in first pairing information, determines whether the second common information is included in second pairing information, and determines pairing failure when the first common information and the second common information are not included in any one of the first pairing information and the second first pairing information.

Figure 13:
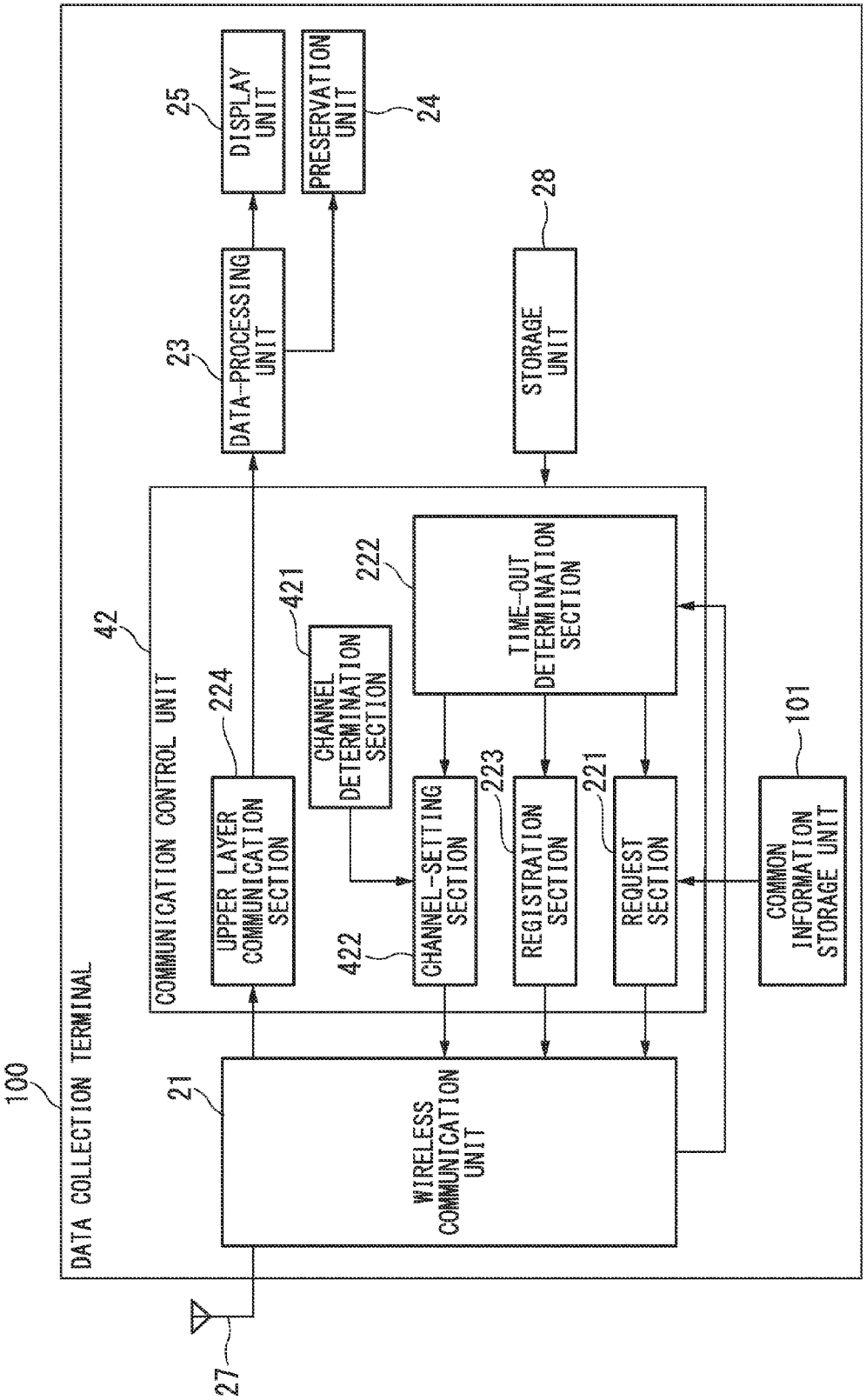
FIG. 13 is a block diagram illustrating the configuration of a data collection terminal in a fifth embodiment of the present invention.

Next, the configuration of a data collection terminal 100 will be described. FIG. 13 is a block diagram illustrating the configuration of the data collection terminal 100 in the present embodiment. In the illustrated example, the data collection terminal 100 includes a wireless communication unit 21, a communication control unit 42, a data-processing unit 23, a preservation unit 24, a display unit 25, an antenna 27, a storage unit 28, and a common information storage unit 101. The data collection terminal 100 includes a battery (not illustrated). The battery supplies power to each element provided in the data collection terminal 100.

The wireless communication unit 21, the communication control unit 42, the data-processing unit 23, the preservation unit 24, the display unit 25, the timer 26, the antenna 27, and the storage unit 28 provided in the data collection terminal 100 are the same as the elements in the second embodiment. The common information storage unit 101 stores in advance the first common information and the second common information that are the same information as that stored in the common information storage unit 91 of the wireless sensing terminal 90. The request section 221 allows the first common information to be included in a first pairing request packet that is generated. The request section 221 allows the second common information to be included in a second pairing request packet that is generated.

Figure 14:
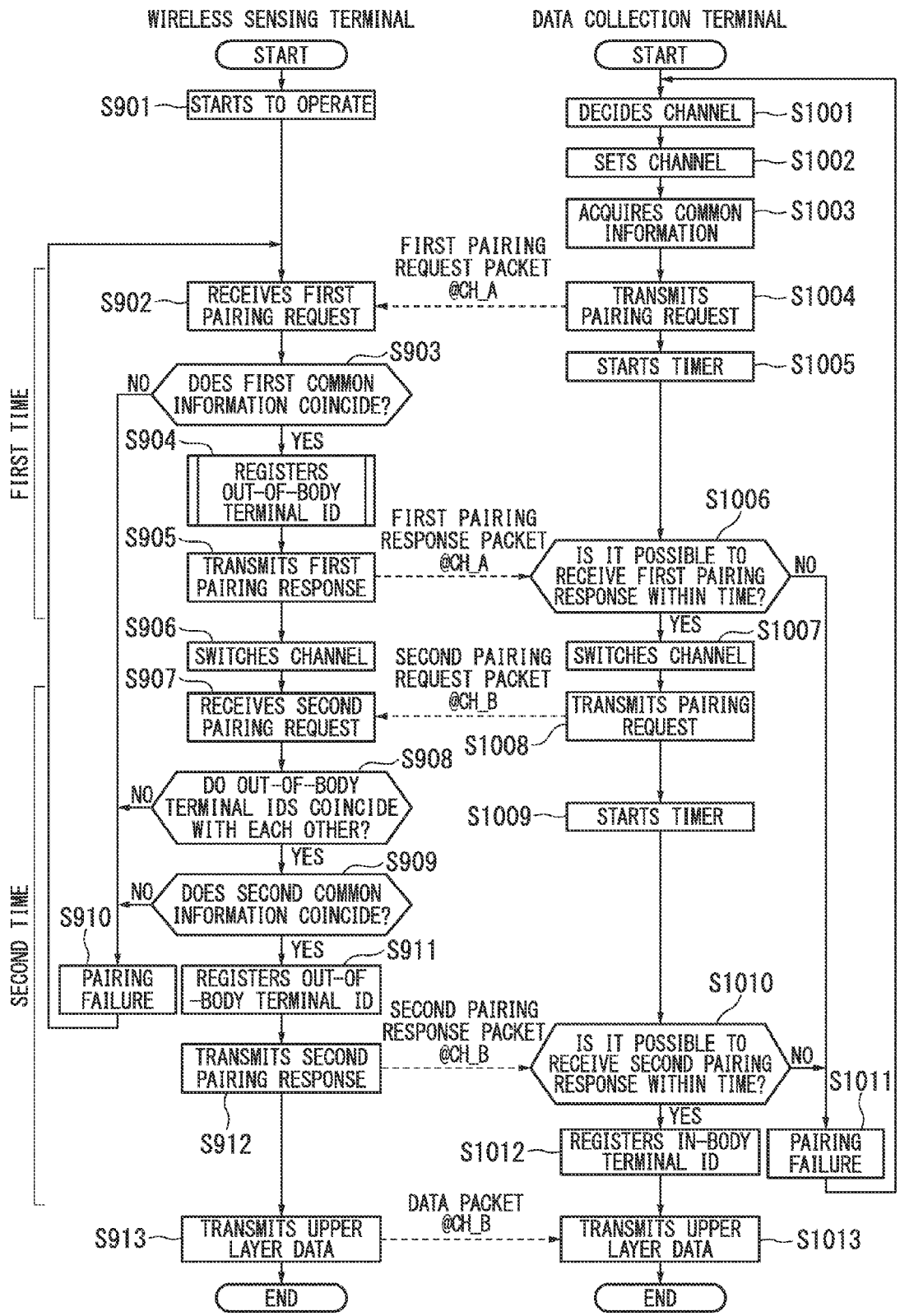
FIG. 14 is a flowchart illustrating an operation procedure between a wireless sensing terminal and a data collection terminal in a fifth embodiment of the present invention.

Next, an operation procedure between the wireless sensing terminal 90 and the data collection terminal 100 will be described. FIG. 14 is a flowchart illustrating the operation procedure between the wireless sensing terminal 90 and the data collection terminal 100 in the present embodiment.

First, the operation procedure of the wireless sensing terminal 90 will be described.

Processes of step S901 and step S902 are the same as those of step S301 and step S302 in the second embodiment.

(Step S903) The determination section 122 determines whether the first common information stored in advance in the common information storage unit 91 coincides with first common information included in the first pairing request packet received in the process of step S902. When the determination section 122 determines that the first common information stored in advance in the common information storage unit 91 coincides with the first common information included in the first pairing request packet received in the process of step S902, the procedure proceeds to a process of step S904.

Otherwise, the procedure proceeds to a process of step S910. The process of step S903 is defined as a first common information check step.

Processes of step S904 to step S908 are the same as those of step S303 to step S307 in the second embodiment.

(Step S909) The determination section 122 determines whether the second common information stored in advance in the common information storage unit 91 coincides with second common information included in the second pairing request packet received in the process of step S907. When the determination section 122 determines that the second common information stored in advance in the common information storage unit 91 coincides with the second common information included in the second pairing request packet received in the process of step S907, the procedure proceeds to a process of step S911. Otherwise, the procedure proceeds to a process of step S910. The process of step S909 is defined as a second common information check step.

Processes of step S910 to step S913 are the same as those of step S308 to step S311 in the second embodiment.

Next, the operation procedure of the data collection terminal 100 will be described.

Processes of step S1001 and step S1002 are the same as those of step S401 and step S402 in the second embodiment.

(Step S1003) The request section 221 acquires the first common information and the second common information that are stored in the common information storage unit 101. Then, the procedure proceeds to the process of step S1004. The process of step S1003 is defined as a common information acquisition step.

(Step S1004) The request section 221 generates a first pairing request packet including the first common information acquired in the process of step S1003, and outputs the first pairing request packet to the wireless communication unit 21. The wireless communication unit 21 transmits the first pairing request packet, which has been input from the request section 221, to the wireless sensing terminal 90 through the antenna 27 using the first channel set in the process of step S1002. Then, the procedure proceeds to a process of step S1005. The process of step S1004 is defined as a first pairing request transmission step.

Processes of step S1005 to step S1007 are the same as those of step S404 to step S406 in the second embodiment.

(Step S1008) The request section 221 generates a second pairing request packet including the second common information acquired in the process of step S1003, and outputs the second pairing request packet to the wireless communication unit 21. The wireless communication unit 21 transmits the second pairing request packet, which has been input from the request section 221, to the wireless sensing terminal 90 through the antenna 27 using the second channel set in the process of step S1007. Then, the procedure proceeds to a process of step S1009. The process of step S1008 is defined as a second pairing request transmission step.

Processes of step S1009 to step S1013 are the same as those of step S408 to step S412 in the second embodiment.

As described above, in the present embodiment, the common information storage unit 91 of the wireless sensing terminal 90 and the common information storage unit 101 of the data collection terminal 100 store the first common information and the second common information. The data collection terminal 100 transmits the first pairing request packet including the first common information to the wireless sensing terminal 90. Then, when the first common information included in the received first pairing request packet does not coincide with the first common information stored in the common information storage unit 91 in advance, the wireless sensing terminal 90 permits no pairing. Similarly, the data collection terminal 100 transmits the second pairing request packet including the second common information to the wireless sensing terminal 90. Then, when the second common information included in the received second pairing request packet does not coincide with the second common information stored in the common information storage unit 91 in advance, the wireless sensing terminal 90 permits no pairing. Consequently, it is possible to further reduce the possibility of a fraudulent connection.

So far, the first embodiment to the fifth embodiment of the present invention have been described in detail with reference to the accompanying drawings. However, detailed configurations are not limited to the embodiments, and designs and the like in the range not departing from the scope of the present invention are included. For example, in the first embodiment to the fifth embodiment, the wireless sensing terminal and the data collection terminal wirelessly communicate with each other in a one-to-one manner. However, the present invention is applicable to relations of 1 to N, M to 1, and M to N (N and M are natural numbers).

The whole or a part of functions of each element provided in the wireless sensing terminal and the data collection terminal in the first embodiment to the fifth embodiment is recorded on a computer-readable recording medium in the form of a program for executing the functions. The program recorded on the recording medium may be read and executed by a computer system. The "computer system" herein is assumed to include an OS or hardware such as a peripheral device.

Furthermore, the "computer-readable recording medium" indicates a portable medium such as a flexible disk, a magnet-optical disc, a ROM, or a CD-ROM, and a storage unit such as a hard disk embedded in the computer system. Moreover, the "computer-readable recording medium" may include a medium for dynamically holding the program for a short time as with a communication line in the case of transmitting the program through a network such as the Internet or a communication line such as a telephone line, a medium for holding the program for a constant time as with a volatile memory in the computer system serving as a server or a client in that case. The program may include a program for executing a part of the aforementioned functions, or a program capable of executing the aforementioned functions through a combination of programs recorded on the computer system.

So far, embodiments of the present invention have been described in detail with reference to the accompanying drawings. However, the present invention is not limited to the embodiments. The present invention may be subject to addition, omission, replacement, and other modifications of the configuration in a range not departing from the scope of the present invention. The present invention is not limited to the abovementioned embodiments but is limited only by the accompanying drawings.

What is claimed is:

1. A wireless communication terminal, in which a packet for requesting pairing in a data link layer is defined as a pairing request packet, comprising:
   a wireless communication unit that performs wireless communication with another terminal;
   a storage device that stores information;
   a storage control unit that stores first identification data included in a first pairing request packet in the storage device when the wireless communication unit receives the first pairing request packet including the first identification data;
   a determination section that determines whether the first identification data stored in the storage device and second identification data included in a second pairing request packet satisfy a condition decided in advance when the wireless communication unit receives the second pairing request packet including the second identification data after the first pairing request packet is received;
   a registration section that registers a terminal, which has wirelessly transmitted the first pairing request packet and the second pairing request packet, as a terminal that wirelessly transmits data of an upper layer above the data link layer when the determination section determines that the first identification data and the second identification data satisfy the condition; and
   a response section that allows the wireless communication unit to transmit a second pairing response packet to the registered terminal when the determination section determines that the first identification data and the second identification data satisfy the condition, the second pairing response packet indicating a response for the second pairing request packet.

2. The wireless communication terminal according to claim 1, further comprising:
   an upper layer communication section that wirelessly transmits the data of the upper layer above the data link layer with the terminal registered by the registration section.

3. The wireless communication terminal according to claim 1, wherein the storage control unit stores a MAC address of the terminal, which has wirelessly transmitted the first pairing request packet, in the storage device as the first identification data, and
   the determination section determines that the first identification data and the second identification data satisfy the condition decided in advance when the second identification data coincides with the first identification data stored in the storage device, the second identification data indicating the MAC address of the terminal having wirelessly transmitted the second pairing request packet.

4. The wireless communication terminal according to claim 1, wherein, when two communication channels with different transmission frequency bands are further defined as a first communication channel and a second communication channel, the storage control unit controls data, which indicates the second communication channel and is included in the first pairing request packet, to be stored in the storage device, in addition to the first identification data.

5. The wireless communication terminal according to claim 1, wherein, when two communication channels with different transmission frequency bands are further defined as a first communication channel and a second communication channel, if the second pairing request packet including the second identification data is received through the second communication channel after the wireless communication unit receives the first pairing request packet, the determination section determines whether the first identification data stored in the storage device and the second identification data included in the second pairing request packet satisfy the condition decided in advance.

6. The wireless communication terminal according to claim 1, wherein, when two communication channels with different transmission frequency bands are further defined as a first communication channel and a second communication channel, the response section allows the wireless communication unit to wirelessly transmit the second pairing response packet through the second communication channel.

7. The wireless communication terminal according to claim 1, wherein, when two communication channels with different transmission frequency bands are further defined as a first communication channel and a second communication channel, the response section allows the wireless communication unit to transmit a first pairing response packet through the first communication channel, the first pairing response packet indicating a response for the first pairing request packet.

8. The wireless communication terminal according to claim 1, wherein, when two communication channels with different transmission frequency bands are further defined as a first communication channel and a second communication channel, the determination section determines whether the first identification data stored in the storage device and the second identification data included in the second pairing request packet satisfy the condition decided in advance only when the second pairing request packet is received within a predetermined time after the wireless communication unit receives the first pairing request packet.

9. The wireless communication terminal according to claim 1, wherein, when two communication channels with different transmission frequency bands are further defined as a first communication channel and a second communication channel, the storage device stores third identification data in advance, and the determination section determines whether the first identification data stored in the storage device and the second identification data included in the second pairing request packet satisfy the condition decided in advance only when the third identification data stored in the storage device coincides with the first identification data included in the first pairing request packet.

10. The wireless communication terminal according to claim 1, wherein, when two communication channels with different transmission frequency bands are further defined as a first communication channel and a second communication channel, the storage device stores fourth identification information and fifth identification information in advance, and the determination section determines whether the first identification data stored in the storage device and the second identification data included in the second pairing request packet satisfy the condition decided in advance only when the fourth identification information stored in the storage device coincides with the fourth identification data included in the first pairing request packet, and the fifth identification information stored in the storage device coincides with the fifth identification data included in the second pairing request packet.

11. A wireless communication terminal, in which a packet for requesting pairing in a data link layer is defined as a pairing request packet, comprising:
a wireless communication unit that performs wireless communication with another terminal;
a storage device that stores information;
a request section that allows the wireless communication unit to wirelessly transmit a first pairing request packet including predetermined identification data, and then to wirelessly transmit a second pairing request packet including the predetermined identification data; and
a registration section that registers a terminal, which has wirelessly transmitted a second pairing response packet, as a terminal that wirelessly transmits data of an upper layer above a data link layer when the wireless communication unit wirelessly transmits the second pairing request packet and then wirelessly receives the second pairing response packet, the second pairing response packet indicating a response corresponding to the second pairing request packet.

12. The wireless communication terminal according to claim 11, further comprising:
an upper layer communication section that wirelessly transmits the data of the upper layer above the data link layer with the terminal registered by the registration section.

13. The wireless communication terminal according to claim 11, wherein the request section allows a MAC address of the wireless communication terminal to be included in the first pairing request packet as first identification data, and allows the MAC address of the wireless communication terminal to be included in the second pairing request packet as second identification data.

14. The wireless communication terminal according to claim 11, wherein, when two communication channels with different transmission frequency bands are further defined as a first communication channel and a second communication channel, the request section allows data indicating the second communication channel to be included in the first pairing request packet, allows the wireless communication unit to wirelessly transmit the first pairing request packet through the first communication channel, and then allows the wireless communication unit to wirelessly transmit the second pairing request packet including the predetermined identification data through the second communication channel.

15. The wireless communication terminal according to claim 11, wherein, when two communication channels with different transmission frequency bands are further defined as a first communication channel and a second communication channel, the storage device stores fourth identification information and fifth identification information in advance, and the request section allows the fourth identification information to be included in the first pairing request packet, and allows the fifth identification information to be included in the second pairing request packet.

16. A wireless communication system, in which a packet for requesting pairing in a data link layer is defined as a pairing request packet, comprising:
a first wireless communication terminal; and
a second wireless communication terminal,
wherein the first wireless communication terminal comprises:
a first wireless communication unit that performs wireless communication with another terminal;
a first storage device that stores information;
a storage control unit that stores first identification data included in a first pairing request packet in the first storage device when the first wireless communication unit receives the first pairing request packet including the first identification data;
a determination section that determines whether the first identification data stored in the first storage device and second identification data included in a second pairing request packet satisfy a condition decided in advance when the first wireless communication unit receives the second pairing request packet including the second identification data after the first pairing request packet is received;
a first registration section that registers a terminal, which has wirelessly transmitted the first pairing request packet and the second pairing request packet, as a terminal that wirelessly transmits data of an upper layer above the data link layer when the determination section determines that the first identification data and the second identification data satisfy the condition; and a response section that allows the wireless communication unit to transmit a second pairing response packet to the registered terminal when the determination section determines that the first identification data and the second identification data satisfy the condition, the second pairing response packet indicating a response for the second pairing request packet, and the second wireless communication terminal comprises:

a second wireless communication unit that performs wireless communication with another terminal;

a second storage device that stores information;

a request section that allows the second wireless communication unit to wirelessly transmit a first pairing request packet including predetermined identification data, and then to wirelessly transmit a second pairing request packet including the predetermined identification data; and a second registration section that registers a terminal, which has wirelessly transmitted a second pairing response packet, as a terminal that wirelessly transmits data of an upper layer above a data link layer when the second wireless communication unit wirelessly transmits the second pairing request packet and then wirelessly receives the second pairing response packet, the second pairing response packet indicating a response corresponding to the second pairing request packet.

17. A wireless communication method, in which a packet for requesting pairing in a data link layer is defined as a pairing request packet, comprising:

a wireless communication step of performing wireless communication with another terminal;

a storage control step of storing first identification data included in a first pairing request packet in a storage device when the first pairing request packet including the first identification data is received in the wireless communication step;

a determination step of determining whether the first identification data stored in the storage device and second identification data included in a second pairing request packet satisfy a condition decided in advance when the second pairing request packet including the second identification data is received after the first pairing request packet is received in the wireless communication step;

a registration step of registering a terminal, which has wirelessly transmitted the first pairing request packet and the second pairing request packet, as a terminal that wirelessly transmits data of an upper layer above the data link layer when it is determined in the determination step that the first identification data and the second identification data satisfy the condition; and a response step of allowing a wireless communication unit to transmit a second pairing response packet to the registered terminal when it is determined in the determination step that the first identification data and the second identification data satisfy the condition, the second pairing response packet indicating a response for the second pairing request packet.

18. A wireless communication method, in which a packet for requesting pairing in a data link layer is defined as a pairing request packet, comprising:

a wireless communication step of performing wireless communication with another terminal;

a request step of allowing a first pairing request packet including predetermined identification data to be wirelessly transmitted, and then a second pairing request packet including the predetermined identification data to be wirelessly transmitted in the wireless communication step; and a registration step of registering a terminal, which has wirelessly transmitted a second pairing response packet, as a terminal that wirelessly transmits data of an upper layer above a data link layer when the second pairing request packet is wirelessly transmitted in the wireless communication step, and then the second pairing response packet is wirelessly received in the wireless communication step, the second pairing response packet indicating a response corresponding to the second pairing request packet.

19. A computer program product embodied on a non-transitory computer readable device to cause a computer to execute, when a packet for requesting pairing in a data link layer is defined as a pairing request packet:

a wireless communication step of performing wireless communication with another terminal;

a storage control step of storing first identification data included in a first pairing request packet in a storage device when the first pairing request packet including the first identification data is received in the wireless communication step;

a determination step of determining whether the first identification data stored in the storage device and second identification data included in a second pairing request packet satisfy a condition decided in advance when the second pairing request packet including the second identification data is received after the first pairing request packet is received in the wireless communication step;

a registration step of registering a terminal, which has wirelessly transmitted the first pairing request packet and the second pairing request packet, as a terminal that wirelessly transmits data of an upper layer above the data link layer when it is determined in the determination step that the first identification data and the second identification data satisfy the condition; and a response step of allowing a wireless communication unit to transmit a second pairing response packet to the registered terminal when it is determined in the determination step that the first identification data and the second identification data satisfy the condition, the second pairing response packet indicating a response for the second pairing request packet.

20. A computer program product embodied on a non-transitory computer readable device, the computer program product to cause a computer to execute, when a packet for requesting pairing in a data link layer is defined as a pairing request packet:

a wireless communication step of performing wireless communication with another terminal;

a request step of allowing a first pairing request packet including predetermined identification data to be wirelessly transmitted, and then a second pairing request packet including the predetermined identification data to be wirelessly transmitted in the wireless communication step; and a registration step of registering a terminal, which has wirelessly transmitted a second pairing response packet, as a terminal that wirelessly transmits data of an upper layer above a data link layer when the second pairing request packet is wirelessly transmitted in the wireless communication step, and then the second pairing response packet is wirelessly received in the wireless communication step, the second pairing response packet indicating a response corresponding to the second pairing request packet.

* * * * *